US012735465B2

(12) United States Patent
Kim et al.

(10) Patent No.: US 12,735,465 B2
(45) Date of Patent: Sep. 15, 2026

(54) METHOD OF PREPARING CIRCULAR PERMUTATION-BASED FUNCTIONAL RECOMBINANT HUMAN-DERIVED FIBROBLAST GROWTH FACTOR 7 AND USE THEREOF

(71) Applicant: INDUSTRY FOUNDATION OF CHONNAM NATIONAL UNIVERSITY, Gwangju (KR)

(72) Inventors: Geun-Joong Kim, Gwangju (KR); Hye-Ji Choi, Hwasun-eup (KR); Dae-Eun Cheong, Gwangju (KR); Su-Kyoung Yoo, Gwangju (KR); Hanui Lee, Jeongeup-si (KR)

(73) Assignee: INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 797 days.

(21) Appl. No.: 18/061,836

(22) Filed: Dec. 5, 2022

(65) Prior Publication Data

US 2023/0340049 A1 Oct. 26, 2023

(30) Foreign Application Priority Data

Apr. 26, 2022 (KR) ........................ 10-2022-0051241

(51) Int. Cl.
*C07K 14/50* (2006.01)
*A61K 38/00* (2006.01)
*C12N 15/70* (2006.01)

(52) U.S. Cl.
CPC .............. *C07K 14/50* (2013.01); *C12N 15/70* (2013.01); *A61K 38/00* (2013.01); *C12N 2800/101* (2013.01)

(58) Field of Classification Search
CPC ...... C07K 14/50; C07K 14/503; C12N 15/70; C12N 2800/101; A61K 38/00; A61K 8/64; A61K 38/1825; A61P 29/00; A61Q 19/00
See application file for complete search history.

(56) References Cited

U.S. PATENT DOCUMENTS 5,858,977 A * 1/1999 Aukerman ............ C07K 14/50 514/6.9
2017/0044228 A1* 2/2017 Alvarez .......... C07K 14/70503

OTHER PUBLICATIONS

Bahadori, Z. et al. "Producing functional recombinant human keratinocyte growth factor in Pichia pastoris and investigating its protective role against irradiation". Enzyme and Microbial Technology, vol. 11 (2018), pp. 12-20. (Year: 2018).*

Bliven, S. et al. "Circular permutation in Proteins". PLOS Computational Biology, vol. 8, No. 3 (2012), p. e1002445. (Year: 2012).*

Buchtova, M. et al. "Instability restricts signaling of multiple fibroblast growth factors". Cellular and Molecular Life Sciences, vol. 72 (2015), pp. 2445-2459. (Year: 2015).*

Schmidt, E. et al. "use of palifermin for the prevention of high-dose methotrexate-induced oral mucositis". Annals of Oncology, vol. 19 (2008), pp. 1644-1649. (Year: 2008).*

Belleudi, F. et al. "FGF7/KGF regulates autophagy in keratinocytes: a novel dual role in the induction of both assembly and turnover of autophagosomes". Autophagy , vol. 10, No. 5 (2014), pp. 803-821. (Year: 2014).*

Zhang, X. et al. "The role of fibroblast growth factor 7 in cartilage development and diseases". Life Sciences, vol. 326 (2023), p. 121804. (Year: 2023).*

Palomares, L.A. et al. "Production of recombinant proteins; Challenges and solutions". Methods in Molecular Biology, vol. 267 (2004), pp. 15-51. (Year: 2004).*

Zheng, Y. et al. "Primer on fibroblast growth factor 7 (FGF 7)". Differentiation, vol. 139 (2024), p. 100801. (Year: 2024).*

Zittersteijn, H.A. et al. "A primer to gene therapy: Progress, prospects, and problems". Journal of Inherited Metabolic Disease, vol. 44 (2021), pp. 54-71. (Year: 2021).*

Ron, D. et al. "Expression of biologically active recombinant Keratinocyte Growth Factor". The Journal of Biological Chemistry, vol. 268, No. 4 (1993), pp. 2984-2988. (Year: 1993).*

NCBI pdf : Human Keratinocyte Growth Factor mRNA, complete cds; GenBank Accession No. M60828.1, Mar. 7, 1995. (Year: 1995).*

Takara Cold Shock Expression System pColdTM DNA manual—Cat # 3360_3364; downloaded from internet at URL: http://www.takara-bio.com, on Dec. 19, 2025. (Year: 2025).*

Korean Intellectual Property Office, Office Action Issued in Application No. 10-2022-0051241, Jul. 29, 2024, 13 pages.

Luo, Y. et al., "Improved production of recombinant fibroblast growth factor 7 (FGF7/KGF) from bacteria in high magnesium chloride," Protein Expression and Purification, vol. 33, No. 2, Feb. 2004, 6 pages.

Jafari, B. et al., "Identification of Novel Single-Domain Antibodies against FGF7 Using Phage Display Technology," SLAS Discovery, vol. 23, No. 2, Feb. 2018, Available Online Aug. 29, 2017, 9 pages.

Kim, Y. et al., "Effective production of human growth factors in *Escherichia coli* by fusing with small protein 6HFh8," Microbial Cell Factories, vol. 20, No. 9, Jan. 7, 2021, 16 pages.

Choi, H. et al., "Circular permutation-based production of functional recombinant human fibroblast growth factor 7," Proceedings of the 17th KSMB Annual Meeting & Symposium, 2021, Nov. 4, 2021, 5 pages. (Submitted as Engish Abstract).

(Continued)

*Primary Examiner* — Nancy J Leith
*Assistant Examiner* — Alexandra Geraldine Dace Denito
(74) *Attorney, Agent, or Firm* — McCoy Russell LLP

(57) ABSTRACT

Provided is a method of preparing a circular permutation (CP)-based functional recombinant human-derived fibroblast growth factor 7 and a use thereof. The fibroblast growth factor 7 to which a circular permutation is applied (CP-$hFGF7^{115-114}$) is independently expressed in a host cell, such that soluble overexpression of the fibroblast growth factor 7 may be induced without causing problems according to the related art, such as lower expression level and stability compared to those of a wild-type hFGF7 protein and amino acid changes in a process of removing a fusion tag.

4 Claims, 6 Drawing Sheets

Specification includes a Sequence Listing.

(56) References Cited

OTHER PUBLICATIONS

Erdag, G. et al., "FGF-7 Expression Enhances the Performance of Bioengineered Skin," Molecular Therapy, vol. 10, No. 1, Jul. 2004, 10 pages.

Gushiken, L. et al., "Cutaneous Wound Healing: An Update from Physiopathology to Current Therapies," Life, vol. 11, No. 7, Jul. 7, 2021, 15 pages.

* cited by examiner

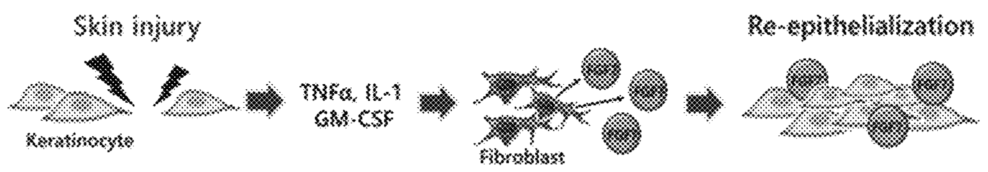
FIG. 1
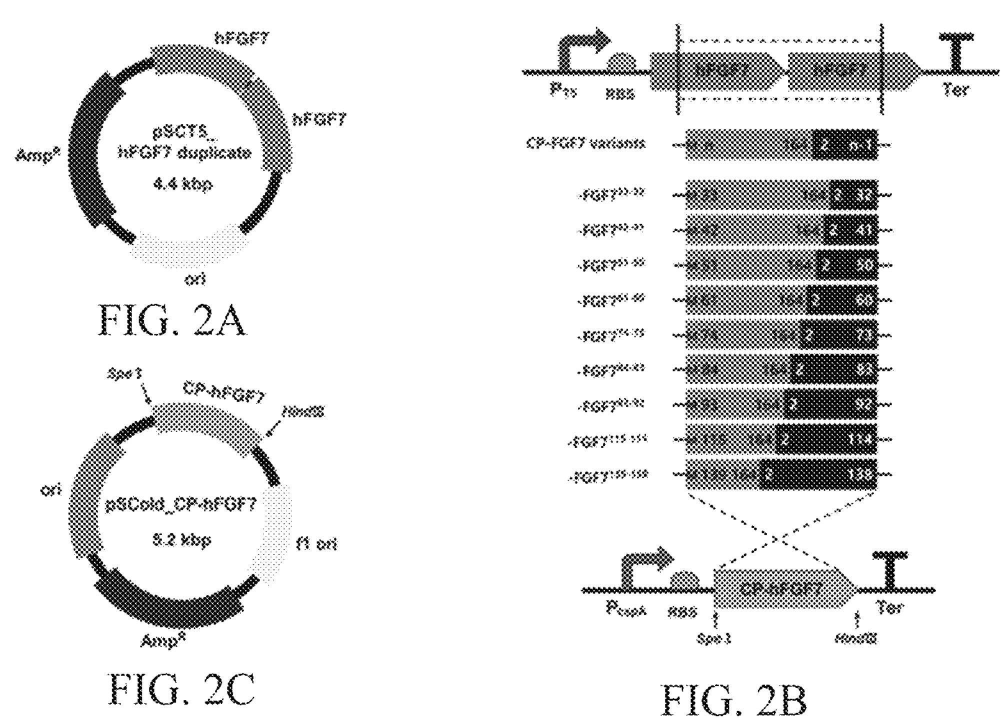
FIG. 2A
FIG. 2C
FIG. 2B
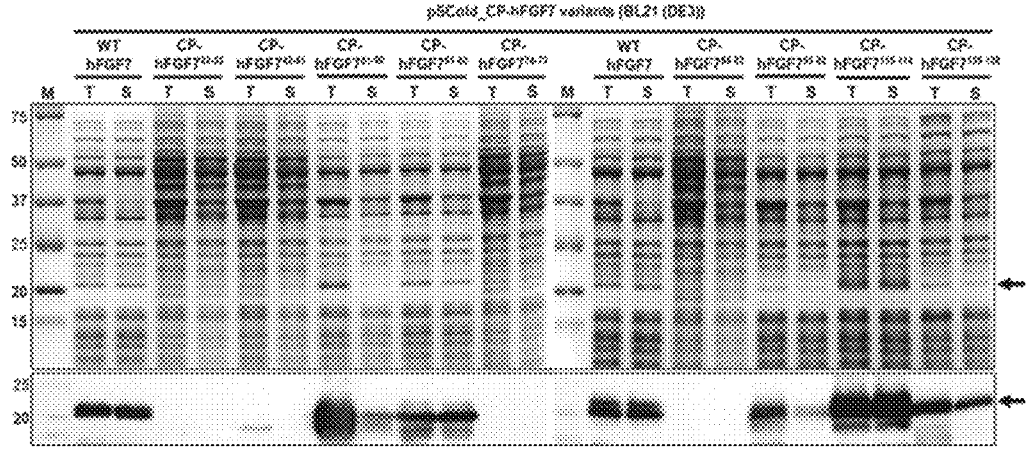
FIG. 3

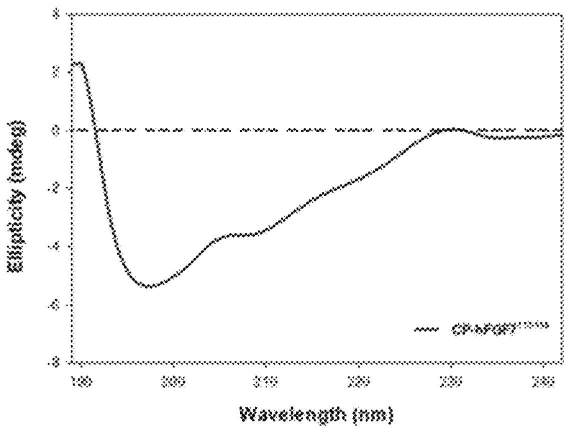
FIG. 8
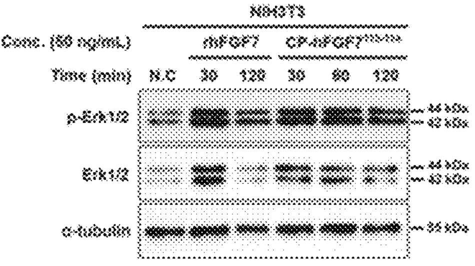
FIG. 9A
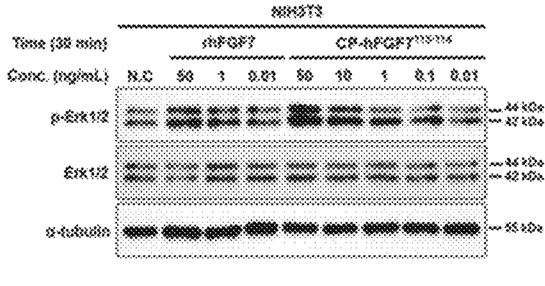
FIG. 9B
Ratio of P-Erk/T-Erk
Concentration (ng/mL)
N.C 50 10 1 0.1 0.01
rhFGF7
CP-hFGF7
FIG. 9C

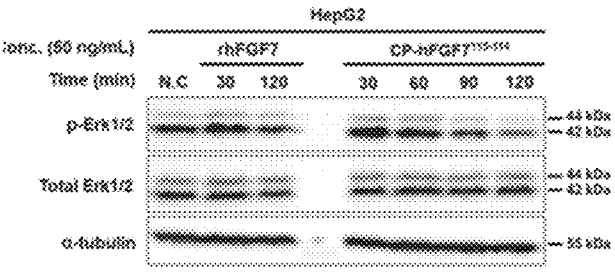
FIG. 10A
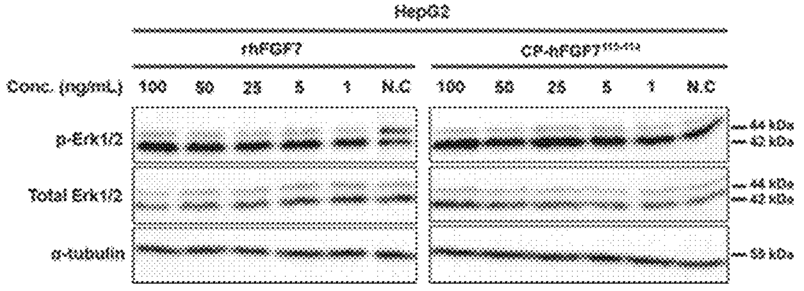
FIG. 10B
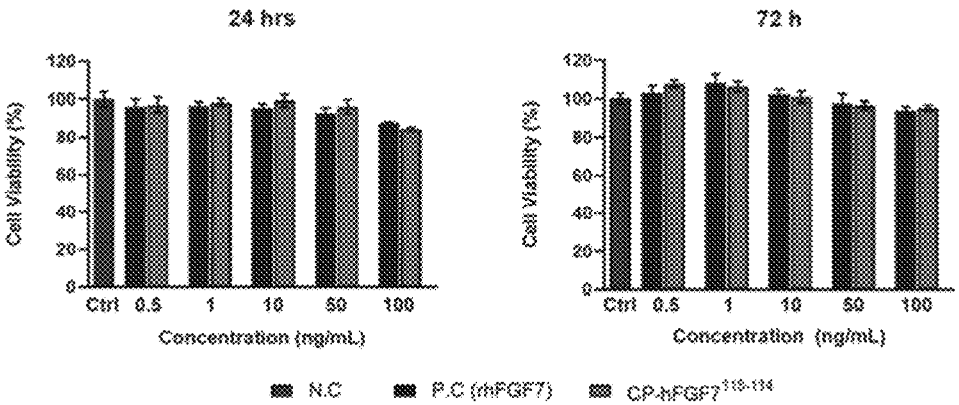
FIG. 11A
FIG. 11B

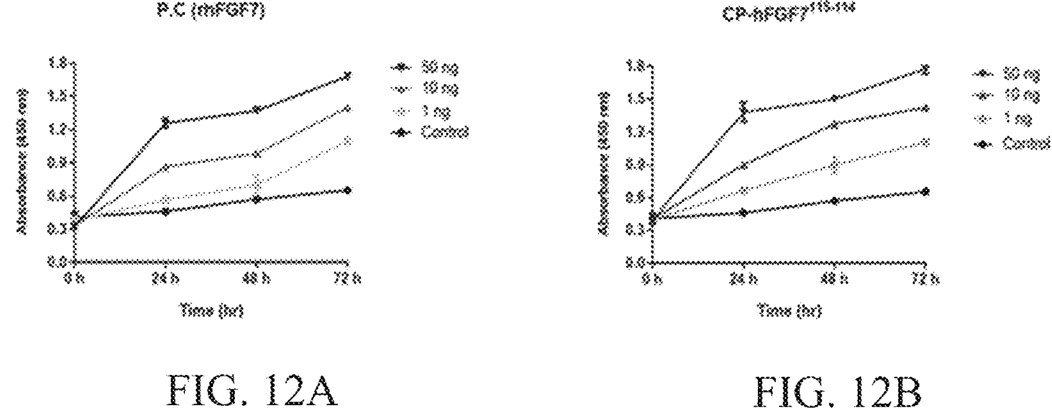
FIG. 12A
FIG. 12B
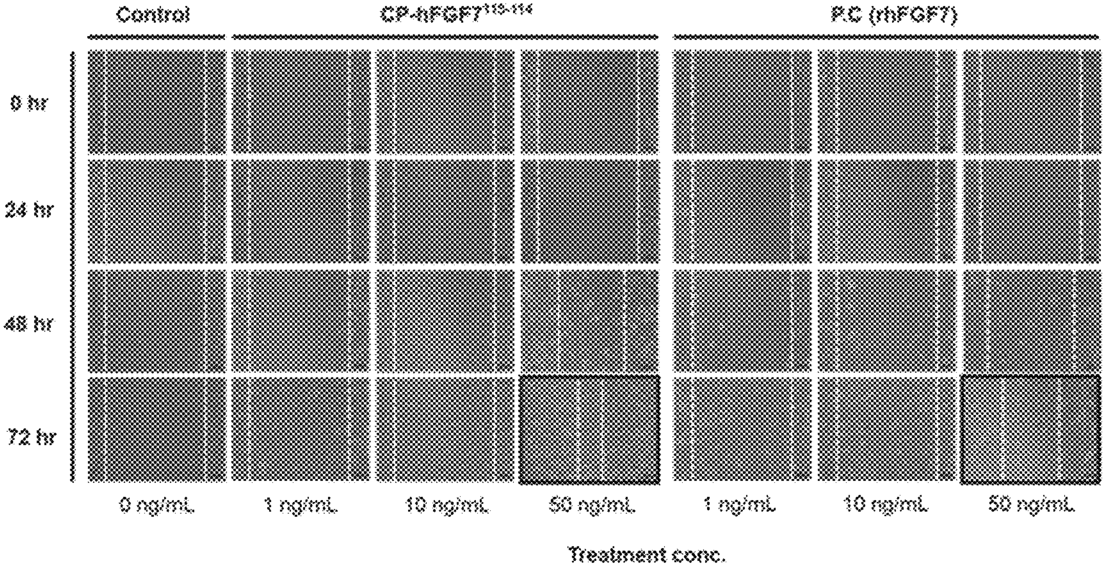
FIG. 13

METHOD OF PREPARING CIRCULAR PERMUTATION-BASED FUNCTIONAL RECOMBINANT HUMAN-DERIVED FIBROBLAST GROWTH FACTOR 7 AND USE THEREOF

CROSS-REFERENCE TO RELATED APPLICATIONS

The present application claims priority to Korean Patent Application No. 10-2022-0051241, filed on Apr. 26, 2022. The entire contents of the above-listed application are hereby incorporated by reference for all purposes.

SEQUENCE LISTING

The material in the accompanying sequence listing is hereby incorporated by reference in its entirety into this application. The accompanying file, named PLS22319_sequence_listing_ST26 was created on Nov. 2, 2022 and is 46 KB.

TECHNICAL FIELD

The following disclosure relates to a method of preparing a circular permutation (CP)-based functional recombinant human-derived fibroblast growth factor 7 and a use thereof, and more particularly, to a nucleic acid sequence encoding an amino acid sequence of a CP-based human-derived fibroblast growth factor 7 (CP-hFGF7) protein variant having significantly improved stability and productivity, a vector containing the nucleic acid sequence, a transformant transformed with the vector, a CP-hFGF7 protein variant expressed in the transformant, a method of preparing the CP-hFGF7 protein variant, a pharmaceutical composition containing the variant, and a cosmetic composition containing the variant.

BACKGROUND

A fibroblast growth factor (FGF) is a representative protein among growth factors that act in cell survival, proliferation, and differentiation, and is known to be widely expressed in cells and tissues. The fibroblast growth factors are divided into paracrine, endocrine, and intracrine FGFs according to an intracellular signaling mechanism, and are a cytokine/hormone family proteins that are divided into 7 subfamilies according to each mode of action, and homology of amino acid sequences, and consists of 22 members. The FGF has a molecular weight of 17 to 34 kDa, and the FGFs present in the same subfamilies have an amino acid homology of 16 to 60%.

A human-derived fibroblast growth factor 7 (hFGF7) is referred to as a keratinocyte growth factor 1 (KGF1), and belongs to an FGF family that acts in a paracrine manner. A paracrine FGF binds to a receptor of an adjacent target cell by secretion of growth factors from mesenchymal-origin stromal cells and is activated through signal transduction.

The fibroblast growth factor (FGF) binds to FGF receptors (FGFRs) (FGFR1b, 1c, 2c, 3b, 3c, and 4), and has multiple functions. The human-derived fibroblast growth factor 7 binds to a high-affinity FGF receptor (FGFR2-IIIb) using heparan sulfate/heparin as a cofactor, and then induces activation of a downstream signaling pathway that transmits a signal from an extracellular space to the inside of the cell (mediating a local signaling response). Among various signaling pathways such as RAS-MAP, PI3K-AKT, and PLCγ, the RAS-MAP kinase pathway is widely known, and tyrosine phosphorylation of a docking protein FRS is induced through FGF/FGFR binding, which acts on nuclear transcription factors through a phosphorylation cascade reaction of GRB2, SOS, and RAS, and plays an important role in regulating biological activities such as cell proliferation, differentiation, tissue repair (wound healing), and liver regeneration.

As an example, in the case of full-thickness wounds of athymic mice, through a report that vascular regeneration occurs rapidly in skin in which hFGF7 is expressed, it has been demonstrated that the hFGF7 described above promotes several important skin wound healing mechanisms (Erdag, G., Medalie, D. A. & Morgan, J. R. (2004), Molecular Therapy, 10(1), 76-85).

In addition, it is known that skin or tissue wounds undergo a healing process including three phases: (i) Inflammatory phase, (ii) Proliferative phase, and (iii) Remodeling phase (Gushiken, L. F. S., Beserra, F. P. & Pellizzon, C. H. (2021), Life, 11(7), 665). Specifically, the healing process includes: (i) Inflammatory phase: hemostasis at wound sites, and acute inflammation through cytokine release and migration of growth factors and leukocytes at the corresponding sites; (ii) Proliferative phase: increases in migration and proliferation of wound keratinocytes, fibroblasts, endothelial cells, and leukocytes, an increase in synthesis of extracellular matrix (ECM), angiogenesis, and re-epithelialization; and (iii) Remodeling phase: replacement of collagen I by collagen III, an increase in activity of matrix metalloproteinase (MNP), and apoptosis of provisional endothelial cells and fibroblasts.

Therefore, the re-epithelialization process in which keratinocytes are activated and proliferation of fibroblasts is increased is important in wound regeneration, which suggests that the hFGF7 may be applied as an active ingredient in a wound medicine. Accordingly, the value and demand for the hFGF7 as a medical protein have increased, and attention has been focused on research on a method for mass production of the hFGF7 at low cost. However, since a human-derived FGF protein having high potential for medical development is often difficult to express, there is an urgent need to develop a technology for solving this problem.

In the related art, in order to produce a recombinant hFGF7 protein by using a bacterial system, various expression and purification methods using (i) expression through codon optimization and (ii) a fusion tag with a protease recognition sequence have been used. In this case, it is required for the hFGF7 protein to contain a signal sequence to act as paracrine in human cells, but the signal sequence is removed to induce expression of recombinant protein in the bacterial cytoplasm. Therefore, a wild-type hFGF7 protein refers here to an hFGF7 protein with no signal sequence. However, in the case of the above method, the problems to be described below cannot be solved, and the development of the novel technology for functional overexpression is urgently needed.

As an example, in the case of (i) the expression through codon optimization, codons of the gene encoding hFGF7 are optimized to increase translation efficiency of a gene in consideration of a codon bias of an *Escherichia coli* host, such that about 3.5 mg/L of hFGF7 is produced with a purity of 92%. However, the problem that the yield should be improved for actual production has been suggested (Jafari, B. & Dastmalchi, S. SLAS DISCOVERY: Advancing Life Sciences R&D, 23(2), 193-201 (2018)).

As an example of the method using (ii) the fusion tag with the protease recognition sequence, a recombinant hFGF7 protein is produced by a method of a GST tag fusion with hFGF7, performing culture by adding 100 mM of magnesium chloride, and removing the tag at the time of purification, such that the yield is improved to a certain level (17 mg/L). However, the recombinant hFGF7 protein is produced in the truncated form (palifermin, currently marketed for treating oral mucositis) in which 24 amino acids at the N-terminus are deleted and thus is shorter than the wild-type hFGF7 (Luo, Y. & McKeehan, W. L. Protein expression and purification, 33(2), 326-331 (2004)).

In addition, it has been reported that an expression level is increased using a 6HFh8 tag obtained by fusing 6 histidines to an 8-kDa peptide derived from *Fasciola hepatica* and an amino acid sequence that recognizes TEV protease, However, unlike natural FGFs, cleavage of this tag from hFGF7 is not complete due to residues (scar) remaining at the N-terminus after TEV protease treatment (Kim Y. S., Kim, Y. C. & Ahn, J. Microbial Cell Factories, 20(1), 1-16 (2021)).

RELATED ART DOCUMENTS

Non-Patent Documents (Non-Patent Document 1) Jafari, B. & Dastmalchi, S. SLAS DISCOVERY: Advancing Life Sciences R&D, 23(2), 193-201 (2018)

(Non-Patent Document 2) Luo, Y. & McKeehan, W. L. Protein expression and purification, 33(2), 326-331 (2004)

(Non-Patent Document 3) Kim Y. S., Kim, Y. C. & Ahn, J. Microbial Cell Factories, 20(1), 1-16 (2021)

SUMMARY

An embodiment of the present disclosure is directed to providing a recombinant circular permutation (CP)-hFGF7 protein having an increased expression level and increased stability while maintaining protein functionality. This is achieved by preparing a protein containing a new terminal sequence by applying a CP method in order to induce amino acid changes at both termini of a protein in which only a translation an order is changed in a form without deletion or mutation of the amino acid in a wild-type hFGF7 protein. Further described is, a method of preparing the CP-hFGF7 protein, and a use of the CP-hFGF7 protein as a pharmaceutical or cosmetic composition.

In one general aspect, a vector contains a polynucleotide encoding a fibroblast growth factor 7 protein variant containing a sequence order by a circular permutation.

The fibroblast growth factor 7 may be a human-derived fibroblast growth factor 7 (hFGF7).

The fibroblast growth factor 7 may consist of a base sequence of SEQ ID NO: 1.

The protein variant may be selected from the group consisting of CP-hFGF7$^{33-32}$, CP-hFGF7$^{42-41}$, CP-hFGF7$^{51-50}$, CP-hFGF7$^{61-60}$, CP-hFGF7$^{74-73}$, CP-hFGF7$^{84-83}$, CP-hFGF7$^{93-92}$, CP-hFGF7$^{115-114}$, and CP-hFGF7$^{139-138}$.

The protein variant may be CP-hFGF7$^{115-114}$.

The polynucleotide encoding the protein variant may consist of a base sequence of SEQ ID NO: 3.

The protein variant may consist of an amino acid sequence of SEQ ID NO: 4.

The polynucleotide may not contain a signal sequence.

The vector may consist of a base sequence of SEQ ID NO: 5.

In another general aspect, there is provided a transformant transformed with the vector.

In still another general aspect, a method of preparing a fibroblast growth factor 7 protein variant includes culturing the transformant to prepare a fibroblast growth factor 7 protein variant.

The transformant may be *Escherichia coli.*

In still another general aspect, a pharmaceutical composition for treating or preventing an inflammation contains, as an active ingredient, a fibroblast growth factor 7 protein variant prepared by the method of preparing a fibroblast growth factor 7 protein variant.

In still another general aspect, a cosmetic composition for treating or preventing an inflammation contains, as an active ingredient, a fibroblast growth factor 7 protein variant prepared by the method of preparing a fibroblast growth factor 7 protein variant.

In still another general aspect, a method for treating an inflammation includes administering the pharmaceutical composition for treating or preventing an inflammation to a subject.

Other features and aspects will be apparent from the following detailed description, the drawings, and the claims.

BRIEF DESCRIPTION OF THE FIGURES

FIG. 1 is a schematic view of a keratinocyte activation response to skin damage.

FIGS. 2A to 2C are schematic views of a vector for expression of a recombinant human-derived fibroblast growth factor 7 protein to which circular permutation logic is applied, in which FIG. 2A illustrates a vector containing a template polynucleotide for securing various circular permutation proteins and prepared in a form of gene duplication (repeat DNA assembly), FIG. 2B illustrates CP1 to CP9-hFGF7 proteins prepared by a specific polymerase chain reaction (PCR) using the vector of FIG. 2A as a template, and FIG. 2C illustrates a vector for expression of a CP-hFGF7 protein.

FIG. 3 illustrates results of SDS-PAGE and western blot analysis for confirming expression aspects of the recombinant human-derived CP1 to CP9-hFGF7 proteins to which the circular permutation is applied in *Escherichia coli* BL21 (DE3), in which WThFGF7 represents a wild-type hFGF7 protein control, M represents a molecular weight size marker, T represents a total fraction of selected CP-hFGF7 proteins, and S represents a fraction of selected soluble CP-hFGF7 proteins.

FIG. 4 illustrates results obtained by expressing a CP-hFGF7$^{115-114}$ protein variant selected from the variants of FIG. 3 in *E. coli* BL21 (DE3) and then purifying the CP-hFGF7$^{115-114}$ protein variant by heparin affinity chromatography, in which the left panel (FIG. 4A) represents heparin affinity chromatography results and the right panel (FIG. 4B) represents SDS-PAGE and western blot results of an elution fraction after purification by heparin affinity chromatography.

FIG. 5D illustrates SDS-PAGE and western blot result of eluted fractions from heparin affinity chromatography, cation exchange chromatography, and size exclusion chromatography.

FIGS. 7A and 7B illustrate results showing structure comparison analysis profiles of the CP-hFGF7$^{115-114}$ protein and the commercially available recombinant hFGF7 (rhFGF7), in which FIG. 7A illustrates a result of confirming a change in absorbance through absorption spectra scanning, and FIG. 7B illustrates a spectral result of analyzing a change in fluorescence emission wavelength.

FIG. 8 illustrates a Far-UV circular dichroism spectroscopy spectrum for secondary structure analysis of the purified CP-hFGF7$^{115-114}$ protein.

FIGS. 9A, 9B, and 9C illustrate results of evaluating activity of the human-derived fibroblast growth factor 7 (CP-hFGF7$^{115-114}$) protein prepared and purified according to the present invention in a mouse embryonic fibroblast cell line (NIH3T3) through ERK phosphorylation, in which FIG. 9A illustrates a result of confirming a phosphorylation level of Erk1/2 over time after treatment with the CP-hFGF7$^{115-114}$ protein at the same concentration of 50 ng/mL, FIG. 9B illustrates a result of confirming a phosphorylation level of Erk1/2 after treatment with the CP-hFGF7$^{115-114}$ protein at various concentrations for 30 minutes, and the right panel of FIG. 9C is a graph obtained by quantifying a ratio of phosphorylation-Erk to total Erk with Image J software.

FIGS. 10A and 10B illustrate results of evaluating activity of the human-derived fibroblast growth factor 7 (CP-hFGF7$^{115-114}$) protein prepared and purified according to the present invention in a human liver cancer cell line (HepG2) through ERK phosphorylation, in which FIG. 10A illustrates a result of confirming a phosphorylation level of Erk1/2 over time after treatment with the CP-hFGF7$^{115-114}$ protein at the same concentration of 50 ng/mL, and FIG. 10B illustrates a result of confirming the phosphorylation level of Erk1/2 after treatment with the CP-hFGF7$^{115-114}$ protein at various concentrations for 30 minutes.

FIGS. 11A and 11B illustrate results of confirming cytotoxicity of the human-derived fibroblast growth factor 7 (CP-hFGF7$^{115-114}$) protein prepared and purified according to the present invention in a mouse embryonic fibroblast cell line (NIH3T3) over time, in which P.C represents a positive control (commercially available recombinant hFGF7 (rhFGF7)).

FIGS. 12A and 12B illustrate results of treating the human-derived fibroblast growth factor 7 (CP-hFGF7$^{115-114}$) protein prepared and purified according to the present invention in a mouse embryonic fibroblast cell line (NIH3T3) at various concentrations for 30 minutes, and then confirming cell proliferation ability over time, in which P.C represents a positive control (commercially available recombinant hFGF7 (rhFGF7)).

FIG. 13 illustrates results of treating the human-derived fibroblast growth factor 7 (CP-hFGF7$^{115-114}$) protein prepared and purified according to the present invention in a mouse embryonic fibroblast cell line (NIH3T3) in which formation of wounds is induced, and then comparing wound healing abilities over time at various concentrations, in which a control group represents commercially available recombinant hFGF7 (rhFGF7).

DETAILED DESCRIPTION

Figures 4A, 4B, 5A, 5B, 5C, 5D:
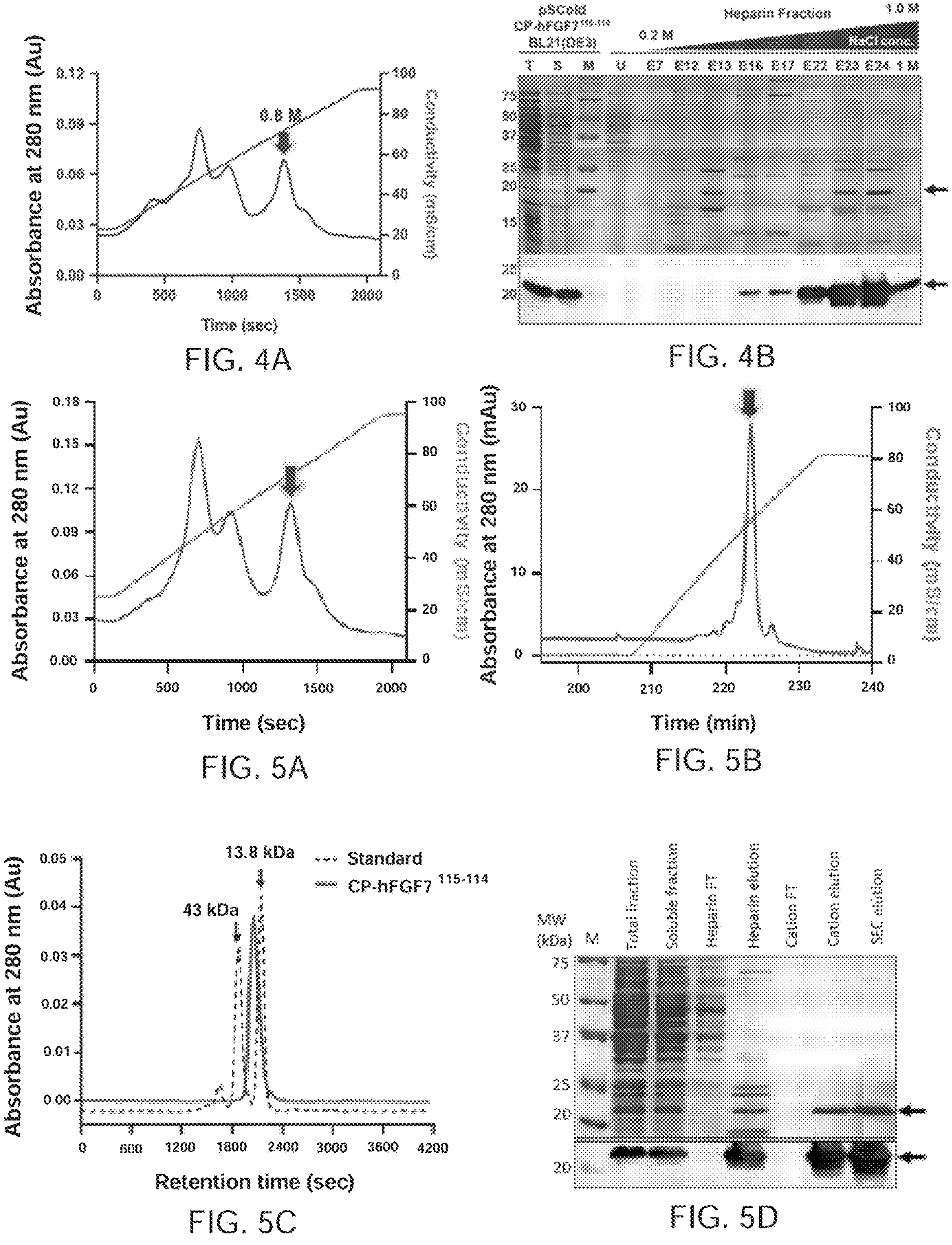
FIGS. 5A to 5D illustrate elution profiles of eluted fractions with a CP-hFGF7$^{115-114}$ protein obtained by sequentially applying heparin affinity chromatography (FIG. 5A), cation exchange chromatography (FIG. 5B), size exclusion chromatography (FIG. 5C), in which ovalbumin (43 kDa) and ribonuclease A (13.8 kDa) are used as molecular weight markers in the size exclusion chromatography.

Hereinafter, a method of preparing a circular permutation (CP)-based functional recombinant human-derived fibroblast growth factor 7 and a use thereof will be described in detail with reference to the accompanying tables and drawings.

The drawings described herein are provided by way of example so that the spirit of the present invention can be sufficiently transferred to those skilled in the art. Therefore, the present invention is not limited to the drawings, and may be implemented in other forms. In addition, the drawings will be exaggerated in order to present the spirit of the present invention.

Terms "first", "second", and the like may be used to describe various elements, but the elements should not be limited by the terms. The terms are only used to distinguish one element from another element. For example, a first element may be named a second element and the second element may also be similarly named the first element without departing from the scope of the present invention.

Technical terms and scientific terms used herein have the general meanings understood by those skilled in the art to which the present invention pertains unless otherwise defined, and a description for the known function and configuration unnecessarily obscuring the gist of the present invention will be omitted in the following description and the accompanying drawings. Terms defined in commonly used dictionaries should be interpreted as having meanings that are consistent with their meanings in a context of the related art, and will not be interpreted as having ideal or excessively formal meanings unless otherwise clearly defined in the present specification.

In addition, unless the context clearly indicates otherwise, singular forms used in the specification of the present invention may be intended to include the plural forms.

In addition, a unit used in the specification of the present invention without special mention is based on weight, and as an example, a unit of % or a ratio refers to wt % or a weight ratio.

In addition, the expression "comprise(s)" used in the specification of the present invention is intended to be an open-ended transitional phrase having an equivalent meaning as "include(s)", "contain(s)", "have (has)", or "is (are) characterized by" and does not exclude an element, a material, or a step that is not further listed. In addition, the expression "consist(s) essentially of" means that a specific element, material, or step that is not listed in combination with another element, material, or step may be present in an amount having no unacceptably significant influence on at least one basic and novel technical idea of the present invention. In addition, the expression "consist(s) of" means the presence of only the listed element, material, or step.

The terms "component", "composition", "composition of compound", "compound", "drug", "pharmacologically active agent", "active agent", "cure", "therapy", "treatment", and "medicine" are used interchangeably to refer to a compound or compounds or a composition of a substance that induces a desired pharmacological and/or physiologic effect by a local and/or systemic action when administered to a subject (human or animal).

The terms "treatment" and "therapy" (as well as different forms thereof) used in the specification of the present invention include preventative (for example, prophylactic), curative, or palliative treatments. The term "treating" used herein includes alleviating or reducing at least one adverse or negative effect or symptom of a condition, disease, or disorder.

The term "sample" or "specimen" used in the present invention refers to a subject for analysis, and is used in the same meaning throughout the specification.

The term "vector", "expression vector", or "recombinant expression vector" used in the specification of the present invention is a linear or circular DNA molecule that includes an element and an additional fragment provided for gene transcription and translation, and encodes a polynucleotide operably linked thereto. The additional fragment includes a promoter, a transcription termination sequence, and the like. The vector, the expression vector, or the recombinant expression vector includes one or more replication origins, one or more selection markers, and the like. The vector, the expression vector, or the recombinant expression vector is generally derived from a plasmid or viral DNA, or contains both elements.

The term "recombinant protein" used in the specification of the present invention refers to a common expression protein that expresses a gene derived from a cell of another species using a heterologous host, and includes a protein in which another protein is linked to an amino or carboxyl terminus of a target protein sequence, or another amino acid sequence is added, if necessary.

An aspect of the present invention relates to a vector or recombinant vector containing a polynucleotide encoding a fibroblast growth factor 7 protein variant containing a new terminal sequence by a circular permutation.

The polynucleotide may be obtained by a circular permutation of a polynucleotide encoding a fibroblast growth factor 7 protein.

In the claims of the present invention and the detailed description of the present invention, the term "by a circular permutation" is used to mean that "a change in order of a base sequence or an amino acid sequence is applied according to a circular permutation method".

The circular permutation refers to a permutation in which elements different from each other are arranged in a circle. An easy-to-understand example thereof includes a case where several people sit around a round table, when the number of elements is n, the number of circular permutations in which n is arranged in a circle is $(n-1)!$. When an arbitrary circular permutation is applied, in a case where the elements are rotated while maintaining the order thereof, the permutations before and after the rotation may be the same as each other, but are not limited thereto. A circular permutation applied to a polynucleotide encoding a protein variant of the present invention may be applied to a site where specific amino acids are contiguous, and specifically, may be applied to a certain number of nucleotides encoding amino acids at a site where they form a loop, but the scope of the present invention is not limited thereto.

As an example, the polynucleotide may not contain a signal sequence, but the present invention is not limited thereto. In human cells, it is required for the fibroblast growth factor 7 protein to contain a signal sequence to act as paracrine. However, in the recombinant expression of the present invention, since the signal sequence is removed to induce expression in the cytoplasm, the wild-type hFGF7 protein in the present invention is used to refer to a protein with no signal sequence.

The vector or the recombinant vector may use a plasmid vector, a cosmid vector, a bacteriophage vector, or a viral vector as a template, but the present invention is not limited thereto. As a preferred example, the vector or the recombinant vector may optionally contain expression control elements such as a promoter, an operator, an initiation codon, a termination codon, a polyadenylation signal, and an enhancer, and may be prepared in various forms depending on a purpose.

The vector or the recombinant vector may contain an antibiotic resistance marker for selection of transformants into which vectors are introduced, and the antibiotic resistance marker may be internal to the vector or may be externally introduced.

The fibroblast growth factor 7 may be a human-derived fibroblast growth factor 7 (hFGF7), but is not limited thereto. As an example, the fibroblast growth factor 7 may contain a base sequence of SEQ ID NO: 1 or may consist of a base sequence of SEQ ID NO: 1.

The protein variant may be selected from the group consisting of CP-hFGF7$^{33-32}$, CP-hFGF7$^{42-41}$, CP-hFGF7$^{51-50}$, CP-hFGF7$^{61-60}$, CP-hFGF7$^{74-73}$, CP-hFGF7$^{84-83}$, CP-hFGF7$^{93-92}$, CP-hFGF7$^{115-114}$, and CP-hFGF7$^{139-138}$, but is not limited thereto. As an example, the protein variant may be CP-hFGF7$^{115-114}$.

As an example, a polynucleotide encoding the CP-hFGF7$^{115-114}$ protein variant may contain a base sequence of SEQ ID NO: 3 or may consist of a base sequence of SEQ ID NO: 3, but the present invention is not limited thereto. The CP-hFGF7$^{115-114}$ protein variant may consist of an amino acid sequence of SEQ ID NO: 4, but the present invention is not limited thereto.

In addition, the vector or the recombinant vector may consist of a base sequence of SEQ ID NO: 5. As an example, the vector or the recombinant vector may be pSCold_CP-hFGF7$^{115-114}$ but is not limited thereto.

Another aspect of the present invention relates to a transformant transformed with the vector or the recombinant vector.

The type of the transformant is not limited as long as the vector of the present invention is introduced and the fibroblast growth factor 7 protein variant may be expressed. As an example, the transformant may be selected from strains belonging to the genus *Escherichia*, the genus *Salmonella*, the genus *Shigella*, the genus *Enterobacter*, the genus *Proteus*, the genus *Pseudomonas*, the genus *Moraxella*, the genus *Helicobacter*, the genus *Stenotrophomonas*, the genus Bdellovibrio, the genus *Legionella*, the genus *Neisseria*, and the genus *Erwnia*. As a specific example, the transformant may be *Escherichia coli*, and more specifically, may be *E. coli* BL21 (DE3).

When the transformant is prepared, a transformation may be performed by a conventional method known to those of skill in the art, and may be performed by, for example, a natural introduction method, a thermal shock method, an electric shock method, or the like, but the present invention is not limited thereto.

Still another aspect of the present invention relates to a method of preparing a fibroblast growth factor 7 protein variant, the method including culturing the transformant to prepare a fibroblast growth factor 7 protein variant. More specifically, the method of preparing a fibroblast growth factor 7 protein variant may include: preparing a vector containing a polynucleotide encoding the fibroblast growth factor 7 protein variant; preparing a transformant by transforming the vector; culturing the transformant to overexpress the fibroblast growth factor 7 protein variant; and recovering overexpressed recombinant proteins, but the present invention is not limited thereto.

When culturing the transformant, culture conditions are not particularly limited, and known culture conditions may be used. As a specific example, the culture may be performed at 14 to 20° C., preferably 15 to 18° C., and more preferably 16° C., and soluble expression of 90% or more of a target protein may be implemented in the above culture temperature range. A medium for culturing microorganisms may also be appropriately introduced from known media, and as an example, a Luria-Bertani (LB) medium may be used, but the present invention is not limited thereto.

When recombinant protein is expressed by the transformant through introduction of the vector, the culture medium may further contain an antibiotic for selecting transformed microorganisms, and may further contain a substance for promoting expression of the protein variant, for example, isopropyl β-D-1-thiogalactopyranoside (IPTG), if necessary, but the present invention is not limited thereto.

The method of preparing a protein variant may be performed by isolating and purifying a protein variant from a culture of the transformant. In this case, the culture may be a transformant or a culture medium thereof, and the culture medium may be a medium containing the transformant or a medium obtained by isolating the transformant.

In addition, the transformant may be disrupted for easy isolation and purification of the protein variant. As a specific method thereof, a method such as physical disruption by ultrasonication or the like or chemical disruption by a surfactant or the like may be used, but the present invention is not limited thereto.

Still another aspect of the present invention relates to a pharmaceutical composition for treating or preventing an inflammation, the pharmaceutical composition containing, as an active ingredient, a fibroblast growth factor 7 protein variant prepared by the method of preparing a fibroblast growth factor 7 protein variant.

The pharmaceutical composition may be formulated into a common formulation in the pharmaceutical field, for example, a formulation for oral administration such as a tablet, a pill, a hard or soft capsule, a liquid, a suspension, an emulsion, a syrup, granules, and an elixir, or a formulation for parenteral administration of a sterile aqueous or oily solvent for intravenous, subcutaneous, sublingual, or intramuscular administration, by adding a common non-toxic pharmaceutically acceptable carrier, excipient, or the like to the active ingredient.

The pharmaceutically acceptable carrier which may be used in the pharmaceutical composition of the present invention is commonly used in formulation, and includes lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, and/or mineral oil, and the like, but the present invention is not limited thereto.

The excipient which may be used in the pharmaceutical composition of the present invention may be a sweetener, a binder, a solubilizer, a solubilizing aid, a wetting agent, an emulsifier, an isotonic agent, an adsorbent, a disintegrant, an antioxidant, a preservative, a lubricant, a filler, a fragrance, or the like, and a ratio and properties of the excipient may be determined depending on solubility and chemical properties of a selected tablet, a selected administration route, and standard pharmaceutical practice. Examples of the excipient include lactose, dextrose, sucrose, mannitol, sorbitol, cellulose, glycine, silica, talc, stearic acid, sterin, magnesium stearate, glyceryl monostearate, magnesium aluminum silicate, starch, gelatin, tragacanth gum, alginic acid, sodium alginate, methyl cellulose, sodium carboxymethyl cellulose, agar, water, ethanol, polyethyleneglycol, polyvinylpyrrolidone, sodium chloride, calcium chloride, orange essence, strawberry essence, and vanilla flavor.

In addition, the pharmaceutical composition of the present invention may be formulated into a parenteral administration form, and in this case, intravenous administration, intraperitoneal administration, intramuscular administration, subcutaneous administration, topical administration, or the like may be used, but the present invention is not limited thereto. In this case, in order to be formulated into a formulation for parenteral administration, the pharmaceutical composition may be prepared into a solution or suspension by mixing the active ingredient with water together with a stabilizer or a buffer, and the solution or suspension may be prepared into a unit dosage form of an ampoule or vial.

In addition, the pharmaceutical composition of the present invention may be sterilized, or may further contain an adjuvant such as a preservative, a stabilizer, a hydrating agent or an emulsifying accelerator, a salt for regulating osmotic pressure, and/or a buffer, may further contain other therapeutically useful materials, and may be formulated according to a conventional method of mixing, granulating, or coating.

Still another aspect of the present invention relates to a health functional food for treating or preventing an inflammation, the health functional food containing, as an active ingredient, a fibroblast growth factor 7 protein variant prepared by the method of preparing a fibroblast growth factor 7 protein variant.

The term "health functional food" refers to a natural material or processed product containing one or more nutrients, and preferably, refers to a food group to which added values are provided to act and express the function of the corresponding food for a specific purpose using a physical, biochemical, or biotechnological method, or the like, or a food designed and processed to sufficiently express the body control function related to the biological defense rhythm control, disease prevention, recovery, and the like of the food composition. The health functional food may contain a cytologically acceptable food supplement additive, and may further contain an appropriate carrier, excipient, or diluent commonly used in preparation of the health functional food.

Examples of the health functional food to which the active ingredient of the present invention may be added include various kinds of foods, beverages, gum, tea, and vitamin complexes. Further, the health functional food includes, but is not limited to, special nutrient foods (for example, milk formulas, infant and baby food, and the like), health supplement foods, confectionary (for example, snacks), dairy products (for example, fermented milk, cheese, and the like), other processed foods, beverages (for example, fruit beverages, vegetable beverages, soybean milk products, fermented beverages, and the like), and the like. The foods, beverages, or food additives described above may be prepared by a common preparation method.

The health functional food of the present invention may contain various nutrients, vitamins, minerals (electrolytes), flavors such as synthetic flavors and natural flavors, coloring agents and fillers (cheese, chocolate, and the like), pectic acid and a salt thereof, alginate and a salt thereof, organic acids, protective colloidal thickeners, pH adjusting agents, stabilizers, preservatives, glycerin, carbonating agents used for carbonated beverages, and the like. These components may be used alone or in combination. For example, the health functional food may contain vitamins A, C, D, E, B1, B2, B6, B12, niacin, biotin, folate, and pantothenic acid, and the like. In addition, the health functional food may contain minerals such as zinc (Zn), iron (Fe), calcium (Ca), chromium (Cr), magnesium (Mg), manganese (Mn), copper (Cu), and rubidium (Rb). In addition, the health functional food may contain amino acids such as lysine, tryptophan, cysteine, valine, and arginine. In addition, the health functional food may contain food additives such as preservatives (potassium sorbate, sodium benzoate, salicylic acid, sodium dehydroacetate, and the like), disinfectants (bleaching powder, higher bleaching powder, sodium hypochlorite, and the like), antioxidants (butylhydroxyanisole (BHA), butylhydroxytoluene (BHT), and the like), coloring agents (tar color and the like), color-developing agents (sodium nitrite, sodium acetate, and the like), bleaching agents (sodium sulfite), seasonings (monosodium glutamate (MSG) and the like), sweeteners (dulcin, cyclamate, saccharin, sodium, and the like), flavors (vanillin, lactones, and the like), swelling agents (alum, potassium D-bitartrate, and the like), fortifiers, emulsifiers, thickeners (adhesive pastes), film-forming agents, gum base agents, antifoaming agents, solvents, and improvers. The additives may be selected and used in an appropriate amount according to the type of food.

As described above, the health functional food of the present invention may have various formulations, in particular, may have any one formulation of powder, granules, a tablet, a capsule, and a beverage, but the present invention is not limited thereto.

Still another aspect of the present invention relates to a cosmetic composition for treating or preventing inflammation, the cosmetic composition containing, as an active ingredient, a fibroblast growth factor 7 protein variant prepared by the method of preparing a fibroblast growth factor 7 protein variant.

The cosmetic composition according to an exemplary embodiment of the present invention may contain a cosmetically or dermatologically acceptable medium or base. The cosmetic composition may be prepared into any topically applicable formulation, for example, a solution, a gel, a solid, an anhydrous paste, an oil-in-water emulsion, a suspension, a micro-emulsion, a microcapsule, a microgranule, an ionic (liposome) or nonionic vesicular dispersion, a cream, a skin softener, a lotion, a powder, an ointment, a spray, or a conceal stick. The cosmetic composition may be prepared according to a conventional method known in the art. The cosmetic composition may be used in the form of an aerosol composition further containing a propellant pressurized in the form of foam.

A formulation of the cosmetic composition is not particularly limited, and may be appropriately selected according to a specific purpose. The cosmetic composition may be prepared into, for example, a formulation such as a skin lotion, a skin softener, a skin toner, a lotion, a lipstick, a lip-gloss, a lip pencil, a milk lotion, a moisture lotion, a nourishing lotion, a massage cream, a nourishing cream, a moisture cream, a hand cream, foundation, an essence, a nourishing essence, a pack, a soap, a cleansing foam, a cleansing lotion, a cleansing cream, a cleansing water, a powder, a body lotion, a body cream, a body oil, a body cleanser, or a body essence.

In the case where the formulation of the present invention is a paste, cream, or gel, animal fibers, vegetable fibers, wax, paraffin, starch, tragacanth, a cellulose derivative, polyethyleneglycol, silicone, bentonite, silica, talc, or zinc oxide may be used as a carrier component.

In the case where the formulation of the present invention is a powder or a spray, a lactose, talc, silica, aluminum hydroxide, calcium silicate, or polyamide powder may be used as a carrier component. In particular, in the case of a spray type formulation, the formulation may further contain a propellant such as chlorofluorohydrocarbon, propane/butane, or dimethylether.

In the case where the formulation of the present invention is a solution or an emulsion, a solvent, a solvate, or an emulsifier may be used as a carrier component. Examples thereof include water, ethanol, isopropanol, ethyl carbonate, ethyl acetate, benzyl alcohol, benzyl benzoate, propyleneglycol, 1,3-butylglycol oil, glycerol aliphatic ester, polyethyleneglycol, or fatty acid ester of sorbitan.

In the case where the formulation of the present invention is a suspension, a liquid diluent such as water, ethanol, or propyleneglycol, a suspension such as ethoxylated isostearyl alcohol, polyoxyethylene sorbitol ester, or polyoxyethylene sorbitan ester, microcrystalline cellulose, aluminum metahydroxide, bentonite, agar, tragacanth, or the like may be used as a carrier component.

In the case where the formulation of the present invention is a surfactant-containing cleansing agent, aliphatic alcohol sulfate, aliphatic alcohol ether sulfate, monoester sulfosuccinate, isethionate, an imidazolinium derivative, methyltaurate, sarcosinate, fatty acid amide ether sulfate, alkyl aminobetaine, aliphatic alcohol, fatty acid glyceride, fatty acid diethanolamide, vegetable oil, a linoline derivative, or ethoxylated glycerol fatty acid ester may be used as a carrier component.

The cosmetic composition may further contain a functional additive and an ingredient contained in a general cosmetic composition. As the functional additive, an ingredient selected from the group consisting of a water-soluble vitamin, a fat-soluble vitamin, a peptide polymer, a polysaccharide polymer, a sphingolipid, and a seaweed extract may be contained.

The cosmetic composition may be mixed with an ingredient contained in a general cosmetic composition together with the functional additive, if necessary. Examples of other ingredients to be mixed include an oil ingredient, a humectant, an emollient, a surfactant, an organic or inorganic dye, an organic powder, an ultraviolet ray absorbing agent, a preservative, an antiseptic, an antioxidant, a plant extract, a pH controller, an alcohol, a pigment, a perfume, a blood circulator, a refrigerant, an antihidrotic, and purified water.

Still another aspect of the present invention relates to a method for treating inflammation, the method including administering the pharmaceutical composition for treating or preventing inflammation to a subject.

In addition, a dosage of the active ingredient in the pharmaceutical composition according to the present invention to mammals including a human may vary depending on a patient's age, weight, or gender, an administration type, a health condition, and a severity of a disease. In general, the active ingredient may be contained in the pharmaceutical composition in an effective dose of 0.001 to 500 mg/kg (weight) per day, and preferably 0.01 to 300 mg/kg (weight) per day. The pharmaceutical composition may be administered once or twice or more per day via an oral or parenteral route. As a specific example, the pharmaceutical composition may be administered to a subject by a method such as oral administration, subcutaneous injection, or subcutaneous application at an interval of 12 hours or longer and 240 hours or shorter, but the present invention is not limited thereto. The dosage may be increased or decreased according to an administration route, severity of a disease, gender, weight, age, and the like. Therefore, the dosage is not intended to limit the scope of the present invention in any way.

Hereinafter, the contents of the present invention will be described in more detail with reference to Examples. Examples are only for illustrating the present invention in more detail, and the scope of the present invention is not limited by Examples.

Strains, Reagents, Materials, and Experimental Protocols

In the present invention, reagents, materials, and protocols used for a polymerase chain reaction (PCR), DNA cloning, transformation, and the like are as follows, which will be apparent to those skilled in the art.

Other reagents were purchased from Sigma-Aldrich (USA) and the like.

Example 1 Preparation and Selection of CP-hFGF7 Variants with Increased Soluble Expression to which Circular Permutation was Applied In order to improve soluble expression of a wild-type hFGF7 protein difficult-to-express in *Escherichia coli*, CP-hFGF7 variants having different amino-termini and carboxyl-termini were prepared by rearranging amino acid sequences of hFGF7.

In order to prepare useable variants, various hFGF7 circular permutation variants were designed by selecting residues in the loop that did not significantly affect protein structure and function, thereby generating new termini.

a. Providing Template by Gene Duplication

As illustrated in the schematic view of FIG. 2A, two hFGF7 genes were fused, and a polymerase chain reaction (PCR) capable of producing a protein with a new terminus was performed by using a plasmid to which gene duplication was introduced in a duplicated gene form as a template and using the primer combination shown in Table 1, wherein REase stands for restriction endonuclease.

TABLE 1

| SEQ ID NO. | Name | Sequence (5'→3') | REase |
|---|---|---|---|
| 6 | pSCT5 hFGF7-Infu-F | TAAAGAGGAGAAAACTAGTATGTGCAATGACATGACTCCAGAG | Infusion |
| 7 | hFGF7-Infu-R | CATTGCAAGTTATTGCCATAGGAAGAAAGTGGG | Infusion |
| 8 | hFGF7(X2)-Infu-F | TGGCAATAACTTGCAATGACATGACTCCAGAGCAAATG | Infusion |
| 9 | pSCT5_hFGF7(X2)-Infu-R | AGCTCAGCTAATTAAGCTTTTAAGTTATTGCCATAGGAAGAAAGTGGGC | Infusion |
| 10 | pSCold Vec-Infu-F | AAGCTTGTCGACCTGCAGTC | Infusion |
| 11 | pSCold_Vec-Infu-R | ACTAGTGGTGTATTACCTCTTAATAATTAAGTGTGC | Infusion |
| 12 | wt-hFGF7-F | AGGTAATACACCACTAGTATGTGCAATGACATGACTCCAGAG | SpeI |
| 13 | wt-hFGF7-R | CTGCAGGTCGACAAGCTTTTAAGTTATTGCCATAGGAAGAAAGTGGG | HindIII |
| 14 | pSCold CP1-hFGF7-F | AGGTAATACACCACTAGTATGGATATAAGAGTGAGAAGACTCTTCTGTC | SpeI |
| 15 | pSCold CP1-hFGF7-R | CTGCAGGTCGACAAGCTTTTACCCTCCTTCCATGTAATCATAACTAGTTATTG | HindIII |
| 16 | pSCold_CP2-hFGF7-F | AGGTAATACACCACTAGTATGCGAACACAGTGGTACCTG | SpeI |
| 17 | pSCold CP2-hFGF7-R | CTGCAGGTCGACAAGCTTTTAACAGAAGAGTCTTCTCACTCTTATATCCC | HindIII |
| 18 | pSCold CP3-hFGF7-F | AGGTAATACACCACTAGTATGAAAAGAGGCAAAGTAAAAGGGACCC | SpeI |
| 19 | pSCold CP3-hFGF7-R | CTGCAGGTCGACAAGCTTTTAATCGATCCTCAGGTACCACTGTG | HindIII |
| 20 | pSCold CP4-hFGF7-F | AGGTAATACACCACTAGTATGAAGAATAATTACAATATCATGGAAATCAGGAC | SpeI |
| 21 | pSCold CP4-hFGF7-R | CTGCAGGTCGACAAGCTTTTACTCTTGGGTCCCTTTTACTTTGC | HindIII |
| 22 | pSCold CP5-hFGF7-F | AGGTAATACACCACTAGTATGGCAGTTGGAATTGTGGCAATCAAAG | SpeI |

TABLE 1-continued

| SEQ ID NO. | Name | Sequence (5'→3') | REase |
|---|---|---|---|
| 23 | pSCold CP5-hFGF7-R | CTGCAGGTCGACAAGCTTTTACACTGTCCTGATTTCCATGATATTGTAATTATTC | HindIII |
| 24 | pSCold CP6-hFGF7-F | AGGTAATACACCACTAGTATGGAAAGTGAATTCTATCTTTGTATGAACAAGGAAGG | SpeI |
| 25 | pSCold CP6-hFGF7-R | CTGCAGGTCGACAAGCTTTTACACCCCTTTGATTGCCACAATTC | HindIII |
| 26 | pSCold_CP7-hFGF7-F | AGGTAATACACCACTAGTATGAAGGAAGGAGAACTCTATGCAAAGAAAG | SpeI |
| 27 | pSCold CP7-hFGF7-R | CTGCAGGTCGACAAGCTTTTAGTTCATACAAAGATAGAATTCACTTTCCACC | HindIII |
| 28 | pSCold CP8-hFGF7-F | AGGTAATACACCACTAGTATGGAAAACCATTACAACACATATGCATCAGC | SpeI |
| 29 | pSCold CP8-hFGF7-R | CTGCAGGTCGACAAGCTTTTACAGAATTAGTTCTTTGAAGTTACAATCTTCATTGC | HindIII |
| 30 | pSCold CP9-hFGF7-F | AGGTAATACACCACTAGTATGCAAAAGGGGATTCCTGTAAGAGGAAAAG | SpeI |
| 31 | pSCold CP9-hFGF7-R | CTGCAGGTCGACAAGCTTTTAATTTAAGGCAACAAACATTTCCCCTC | HindIII |

A pair of primers of SEQ ID NOs: 6 and 7, a pair of primers of SEQ ID NOs: 8 and 9, the primer being designed to contain hFGF7 used as inserts for homologous recombination to be a duplicated gene, and pET24a_hFGF7 (provided by Korea Institute of Ocean Science & Technology) used as a template were mixed, and amino acids at positions from 32 to 194 of the human-derived fibroblast growth factor 7 excluding the signal sequence were amplified by PCR.

The PCR product (insert) and a linearized pSCT5 vector cleaved with SpeI and Hind III were ligated using an In-Fusion® HD cloning kit (Clontech) recognizing and fusing about 15 homologous base sequences at the insert terminus and the vector terminus.

The plasmid of FIG. 2A prepared by the above method was used as a template, and CP1 to CP9-hFGF7 were amplified with pairs of primers corresponding to SEQ ID NOs: 14 to 31, followed by cleavage with Spe I and Hind III restriction enzymes. A translation enhancing element (TEE), a His tag and a factor Xa cleavage sequence in a pCold™ I vector (Takara) were removed for independent expression of a circular permutation variant.

In order to perform cloning of the various prepared inserts (CP1 to CP9-hFGF7), a new pSCold vector to which restriction enzyme sites (Spe I and Hind III) were added to a pair of primers of SEQ ID Nos. 10 and 11 was prepared. After the treatment of pSCold vector with Spe I and Hind III restriction enzymes, CP1 to CP9-hFGF7 DNA (inserts) and the pSCold vector were ligated with T4 DNA Ligase (Thermo Fisher Scientific (Waltham, MA, USA)) at 4° C. for 16 hours, and then were transformed into *E. coli* XL1-Blue as a cloning host. As a control group, a recombinant vector with a wild-type gene prepared in the same manner using a pair of primers of SEQ ID NOs. 12 and 13 was used.

Thereafter, the plasmid was purified with a mini-prep kit (Nucleospin® Plasmid EasyPure, MN), and then, the purified plasmid was transformed again into *E. coli* BL21 (DE3) as an expression host.

The expression host was plated on a Luria-Bertani (LB) solid medium to which 100 μg/mL of ampicillin (Amp) was added and then was cultured to produce CP1 to CP9-hFGF7 proteins (see FIGS. 2B and 2C).

b. Confirmation and Comparison of Expression Level of CP1 to CP9-hFGF7 Proteins

Single colonies of the cultured *E. coli* BL21 (DE3) were inoculated into 3.5 mL of an LB medium (10 g/L of NaCl, 10 g/L of tryptone, and 5 g/L of yeast extract), and then, culture was performed under stirring at 37° C. and 235 rpm.

When an absorbance ($OD_{600}$) measured at 600 nm reached 2.0, 70 μL of a culture medium was re-inoculated into 3.5 mL of a new LB medium with the same composition. When the culture was performed under stirring at 37° C. and 235 rpm and an absorbance reached 0.6, isopropyl-β-D-thiogalactopyranoside (IPTG) was added to induce protein expression. After the addition of IPTG, protein expression was induced while additional culture was performed under stirring at 16° C. and 200 rpm for 30 hours.

After completion of the culture, the culture medium was corrected to have an absorbance of 2.0, and then, the culture medium was centrifuged at 4° C. and 13,000 rpm for 2 minutes to obtain pellets. The resulting pellets were suspended in a 10 mM sodium phosphate buffer solution (pH 7.3) and lysed by irradiating the cells with ultrasonic waves three times for 2 seconds. The lysed cells (Total; T) was centrifuged at 4° C. and 13,200 rpm for 25 minutes to obtain a soluble supernatant (Soluble; S) fraction from which an insoluble aggregate was removed.

A 5× sample loading buffer (0.225 M of Tris-HCl, pH 6.8, 50% glycerol, 5% SDS, 0.005 M of bromophenol blue, and 10% 2-mercaptoethanol) was added to the samples obtained in each step at a ratio of 4:1, the sample was heated at 100° C. for 15 minutes to induce protein denaturation, and the samples was subjected to electrophoresis with 10% tricine-SDS-PAGE.

The results are illustrated in FIG. 3.

Among the confirmed CP-hFGF7 variants, a CP-hFGF7$^{115-114}$ protein, which was soluble overexpressed in comparison to a wild-type protein, was selected and used for a subsequent experiment.

Example 2 Purification of Soluble Overexpressed CP-hFGF7$^{115-114}$ Protein

The circular permutation-based fibroblast growth factor 7 (CP-hFGF7$^{115-114}$) protein secured in Example 1 was subjected to three successive stages of chromatography using a HiTrap heparin HP column, cation exchange chromatography using an SP-Sepharose column, and size exclusion chromatography using a Superdex 200 (10/300, GL) column.

2.1. Culture and Storage of Recombinant Cells

After pre-culture of a small amount of cells was performed in a test tube, recombinant cells were obtained by using a flask culture for purification.

Specifically, a gene sequence of SEQ ID NO: 3 encoding a CP-hFGF7$^{115-114}$ protein was introduced into a pSCold vector to prepare a pSCold_CP-hFGF7$^{115-114}$ vector (SEQ ID NO: 5), the pSCold_CP-hFGF7$^{115-114}$ vector was transformed into an *E. coli* BL 21 (DE3), and then, the transformed cell was plated on an LB agar solid medium containing ampicillin.

A single colony grown on the solid medium was inoculated into 3.5 mL of an LB liquid medium containing 100 μg/mL of ampicillin and cultured at 37° C. and 235 rpm for 5 to 6 hours. The resulting 2 mL of a pre-culture was re-inoculated into 200 mL of an LB medium containing 100 μg/mL of ampicillin, and culture was performed under the same conditions until an absorbance ($OD_{600}$) measured at 600 nm reached 0.6.

Thereafter, the culture was induced by adding IPTG and further incubated at 16° C. and 200 rpm for 30 hours, cells were obtained by centrifugation at 4° C. and 6,000 rpm for 10 minutes, and then, the resulting cells were stored at −20° C. and used for a subsequent experiment.

2.2 Purification of Protein 2.2.1. Heparin Affinity Chromatography

The frozen cell pellets were subjected to freezing and thawing twice. The cells were then suspended in 60 mL of a lysis buffer solution (20 mM of sodium phosphate, pH 6.5), irradiated with ultrasonic waves at 42% of intensity for 2 seconds. The irradiation was stopped for 8 seconds and was repeated for 12 minutes to lyse the cells.

The cell lysate (Total: T) was centrifuged at 4° C. and 10,000 rpm for 80 minutes to separate a supernatant (S) from which an insoluble aggregate was removed. The separated supernatant was loaded on a heparin column equilibrated with a mobile phase buffer (20 mM of sodium phosphate, 0.2 M of NaCl, pH 6.5) at a flow rate of 0.5 mL/min, and washing was sufficiently performed with the mobile phase buffer at a flow rate of 1 mL/min for 40 minutes.

Thereafter, an elution buffer (20 mM of sodium phosphate, 1 M of NaCl, pH 6.5) was used to induce an increase in NaCl concentration gradient from 0.2 to 1 M, and an eluted CP-hFGF7$^{115-114}$ protein was harvested by using fraction collector.

Among the obtained fractions, a fraction having an absorbance at 280 nm was analyzed by SDS-PAGE.

The results are illustrated in FIG. 4A and FIG. 4B.

It was confirmed from the results that a CP-hFGF7$^{115-114}$ protein was obtained at 0.75 to 0.85 M of NaCl. This result indicates that the CP-hFGF7$^{115-114}$ protein was improved in a form with increased heparin binding affinity, unlike that the wild-type hFGF7 protein was eluted at 0.5 to 0.6 M of NaCl.

2.2.2. Cation Exchange Chromatography

Thereafter, fractions containing the CP-hFGF7$^{115-114}$ protein were collected and mixed with a binding buffer solution (20 mM of sodium phosphate, pH 7.3) at a volume ratio of 1:1, and then, the mixture was loaded on an SP-Sepharose column equilibrated with a binding buffer solution at a flow rate of 0.5 mL/min.

After completion of the loading, 80 mL of an elution buffer (20 mM of sodium phosphate, 1 M of NaCl, pH 7.3) was used to induce an increase in NaCl concentration gradient from 0 to 1 M, and an eluted CP-hFGF7$^{115-114}$ protein was harvested by using fraction collector.

As a result, it was confirmed that the CP-hFGF7$^{115-114}$ protein was eluted at about 0.7 M of NaCl.

2.2.3. Size Exclusion Chromatography 1 mL of the CP-hFGF7$^{115-114}$ protein obtained by the cation exchange chromatography were injected into a Superdex® 200 (10/300, GL) column equilibrated with a mobile phase buffer (20 mM of sodium phosphate, 0.4 M of NaCl, pH 7.3) at a flow rate of 0.5 mL/min. At this time, ovalbumin (43 kDa) and ribonuclease A (13.8 kDa) were used as protein molecular weight markers.

After completion of the injection, as a result of measuring a retention time (RT) of the CP-hFGF7$^{115-114}$ protein, the measured retention time was 34 minutes, and it was confirmed that a molecular weight of the CP-hFGF7$^{115-114}$ protein was about 19 kDA and the CP-hFGF7$^{115-114}$ protein was a monomer.

The isolation results using the three stages of chromatography are illustrated in FIGS. 5A to 5D.

From the Tricine-SDS-PAGE results, it was confirmed that the high-purity CP-hFGF7$^{115-114}$ protein was obtained by the three stages of successive column purification process.

Example 3 Quantification and Yield of Purified CP-hFGF7$^{115-114}$ Protein

The purity of the protein purified by Example 2 was measured by Tricine-SDS-PAGE and western blot, and the total protein concentration was measured as follows by a Bradford method using bovine serum albumin (BSA) as a standard protein.

First, 5 μL of a purified protein prepared at each of 5-fold and 10-fold dilutions and 155 μL of a Bradford reagent were mixed in a 96-well plate to induce a reaction at room temperature for 5 minutes while blocking light, and a concentration of the purified protein was measured at 595 nm with a microplate reader (TECAN).

As a result, a purification yield of about 6 to 7 mg based on 1 L of a flask cell culture medium was obtained. It was confirmed from this result that the yield of the CP-hFGF7$^{115-114}$ protein was increased by about 2 times the yield of 3.5 mg/L of the wild-type hFGF7 protein reported in the related art.

A recovery yield of the soluble expressed protein was around 12%, such that a yield of 40 mg or more could be expected in an optimized process. That is, it was confirmed that the productivity of the soluble expressed protein according to the present invention was significantly increased by 11 to 12 times the productivity obtained by a method according to the related art.

Example 4 Comparison of Storage Stabilities Between the Wild-Type (hFGF7) and Purified CP-hFGF7$^{115-114}$ Protein In order to perform comparison of storage stability between the purified CP-hFGF7$^{115-114}$ and a commercially available recombinant human-derived fibroblast growth factor 7 (rhFGF7) (PeproTech), both proteins were refrigerated under the same condition at 4° C., and the storage stability was compared by Tricine-SDS-PAGE after 35 days of incubation.

Figure 6:
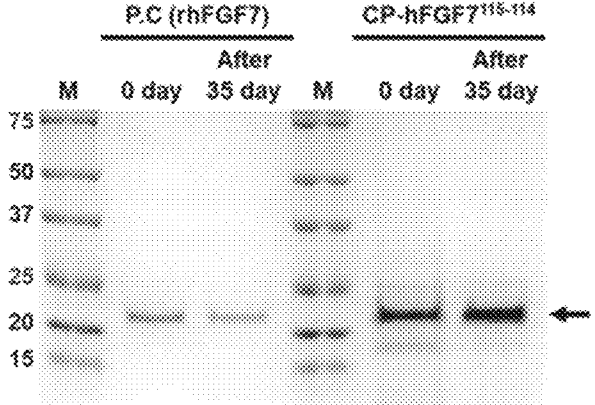
FIG. 6 illustrates a result of confirming stability of the purified CP-hFGF7$^{115-114}$ protein from the SDS-PAGE analysis result for confirming low-temperature storage stability at 4° C., in which M represents a molecular weight size marker and P.C represents a positive control (commercially available recombinant hFGF7 (rhFGF7)).

The results are illustrated in FIG. 6.

It was confirmed from the results that in the case of the purified protein according to the present invention, the stability was significantly more improved than that of the wild-type hFGF7 protein.

Example 5 Comparison of Structures of Wild-Type (hFGF7) and Purified CP-hFGF7$^{115-114}$ Protein 5.1 UV-Vis Absorption Spectra Scanning In order to analyze a related structure of the purified protein to the function, spectral properties of the purified protein and the wild-type protein were compared using a UV-vis absorption scanning method.

UV-vis absorption scanning was performed on the purified proteins obtained as described in the Examples, using a buffer solution (20 mM of sodium phosphate, 0.4 M of NaCl, pH 7.3) as a negative control, and a commercially available recombinant human-derived fibroblast growth factor 7 (rhFGF7) (PeproTech) as a positive control. The difference in absorption wavelength was measured.

A change in absorption spectrum was measured in a quartz cuvette using 100 of the sample from each of the experimental groups while changing a wavelength from 260 nm to 600 nm at an interval of 5 nm.

Figure 7A:
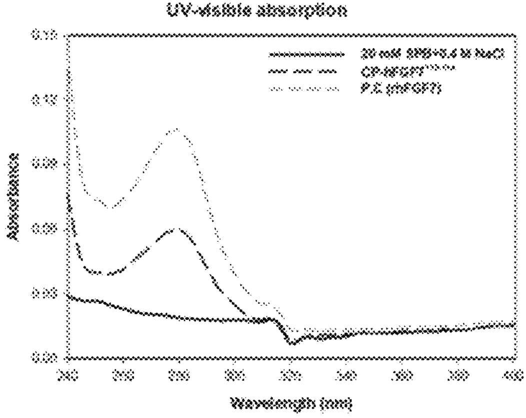

The results are illustrated in FIG. 7A.

It was confirmed from the results that the purified protein and the positive control had the same max value of 280 nm, which showed that the structure of the purified protein according to the present invention prepared by application of a circular permutation was not significantly different from that of the wild-type protein. For reference, the difference in absorbance intensity value in FIG. 7A is a result of the fact that the concentrations of the used proteins were 200 μg/mL for the positive control group and 150 μg/mL for the purified protein.

5.2 Fluorescence Emission Wavelength Scanning

In order to analyze the structure of the purified protein related to the function, a fluorescence emission wavelength scanning method was also conducted to compare the wild type and the purified proteins.

Figure 7B:
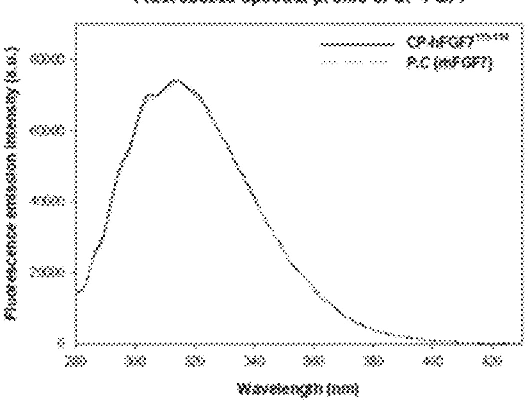

A change in fluorescence emission wavelength of each 150 μg/mL of the positive control rhFGF7 and the purified CP-hFGF7$^{115-114}$ protein was measured at an excitation wavelength of 250 nm and an interval of 3 nm. The results are illustrated in FIG. 7B.

It could be presumed from the results that there was no significant difference between the spectra of the purified protein and the positive control group, and the structure of the purified CP-hFGF7$^{115-114}$ protein was not significantly different from that of the wild-type hFGF7 protein.

5.3 Circular Dichroism (CD) Spectroscopy

In order to compare the structures of the purified protein and the wild-type FGF7 protein, secondary structure analysis of the CP-hFGF7$^{115-114}$ variant was performed by circular dichroism (CD) spectroscopy.

Salts such as NaCl contained in the purified protein were removed by a PD-10 column using a buffer solution (10 mM of sodium phosphate, 0.1 M of NaCl, pH 7.3), and then analysis was performed.

An average of values obtained by performing three measurements of a wavelength between 190 to 260 nm at an interval of 0.1 nm, 25° C., and a scanning rate of 100 nm/min using JASCO-1500 (Jasco Inc., using the device of Korea Basic Science Institute (KBSI)) was used (see FIG. 8).

As illustrated in FIG. 8, it may be observed that CP-hFGF7$^{115-114}$ has a maximum negative absorption band at 195 nm and 210 to 200 nm, which are characteristics bands of random coil and β-sheet structures, and detailed ratios of secondary structures are shown in Table 2. Comparing the reported results from a previous report (Jafari, B. & Dastmalchi, S. SLAS DISCOVERY: Advancing Life Sciences R&D, 23(2), 193-201 (2018)), it may be confirmed that there is a slight difference in composition ratio of the secondary structure. The difference is expected due to the fact that in the previously reported CD spectroscopy of FGF7, a buffer solution (10 mM of phosphate buffer, pH 7.0) and FGF7 in which 6 histidines and thrombin cleavage recognition sequences (when the corresponding region is analyzed for a secondary structure, an α-helical structure is expected) are fused to the amino terminal region are different. Nevertheless, the fact that there is no significant difference in content in the main secondary structures (random coli and β-sheet structures) derived from the two results indicates that the both proteins have high structural similarity.

The reason for this is that although there is a slight difference in value of CD spectroscopy due to the protein composition and the buffer solution in the compared document, as can be seen in Examples 5-1 and 5-2, the characteristics of absorption and fluorescence emission spectra closely linked with three-dimensional structural characteristics are significantly similar. This fact may also be presumed from the measurement results of the activity that is more related to the structure (see Example 6).

TABLE 2

| | Second structure (%) | | | |
|---|---|---|---|---|
| | % α-helical | % β-sheet | % Turn | % Random coil |
| FGF7 (Jafari, B. et. al.) | 4.95 | 41.05 | 0.0 | 54 |
| CP-hFGF7$^{115-114}$ | 0.0 | 44.8 | 6.4 | 48.8 |

Example 6 Activation of Signaling Pathway by Purified CP-hFGF7$^{115-114}$ Protein In order to confirm whether a MARK signaling pathway was activated through Erk phosphorylation on a Ras-Raf-Erk1/2 MARK pathway in a mouse embryonic fibroblast cell line (NIH3T3) and a human liver cancer cell line (HepG2), the two cell lines were treated with the recombinant hFGF7, and then, immunoblotting was performed.

6.1 NIH3T3 Cell Line-Based Assay

A mouse embryonic fibroblast cell line (NIH3T3) was inoculated into a DMEM (Gibco, ThermoFisher Scientific (Waltham, MA, USA)) medium containing 10% bovine calf serum (BCS), 100 μg/mL of penicillin, and 100 μg/mL of streptomycin, the mouse embryonic fibroblast cell line was cultured in an incubator at 37° C. and 5% $CO_2$, the mouse embryonic fibroblast cell line was equally dispensed to a 6-well cell culture plate at $2\times10^5$ cell/well, and then, the mouse embryonic fibroblast cell line was further cultured for two days.

Thereafter, before the purified CP-hFGF7$^{115-114}$ protein was treated, cell starvation was performed in a serum-free DMEM medium containing no fetal bovine serum (FBS) for 24 hours.

After quantification was performed by the method described in Example 3, experimental groups were classified into experimental groups obtained by treating NIH3T3 cell line experimental groups with 50 ng/mL of the purified CP-hFGF7$^{115-114}$ protein for 30 minutes, 60 minutes, and 120 minutes, and experimental groups obtained by treating the NIH3T3 cell line experimental groups with the CP-hFGF7$^{115-114}$ protein at treatment concentrations of 50, 10, 1, 0.1, and 0.01 ng/mL. Thereafter, the experimental groups were treated with a RIPA buffer solution (25 mM of Tris-HCl, pH 7.6, 150 mM of NaCl, 1% NP-40, 1% sodium deoxycholate, 0.1% SDS, Thermo Fisher Scientific (Waltham, MA, USA)) containing protease inhibitor cocktail (Thermo Fisher Scientific (Waltham, MA, USA)) and phosphatase inhibitor cocktail (Thermo Fisher Scientific (Waltham, MA, USA)) to lyse cells.

Subsequently, a cell lysate was obtained with a scraper, and then, immunoblotting using antibodies against Erk1/2 (Cell Signaling Technology Co. (Danvers, MA, USA)), phosphorylated Erk1/2 (Cell Signaling Technology Co. (Danvers, MA, USA)), and α-tubulin (Santa Cruz Biotechnology Inc. (Dallas, TX, USA)) was performed to analyze activity.

The results are illustrated in FIGS. 9A, 9B, and 9C.

The treatment concentrations of the purified protein and the positive control group were fixed at 50 ng/mL, and then, the treatment time was at 30 minutes, 60 minutes, and 120 minutes. As a result, strong phosphorylation of Erk1/2 was induced with short-term treatment for 30 minutes, and the Erk1/2 phosphorylation was decreased over time, which was the same as that of rhFGF7 as the positive control group (see FIG. 9A).

In addition, the treatment concentration of the protein was changed to 50, 10, 1, 0.1, and 0.01 ng/mL, and the same treatment time was set to 30 minutes. As a result, the Erk1/2 phosphorylation was decreased in a concentration-dependent manner of the treated purified protein. It was confirmed that the level was similar to that of the positive control group treated at the same concentration (see FIG. 9B and FIG. 9C).

6.2 HepG2 Cell Line-Based Assay

A human liver cancer cell line (HepG2) was inoculated into a DMEM (Gibco, ThermoFisher Scientific (Waltham, MA, USA)) medium containing 10% fetal bovine serum (FBS), 100 μg/mL of penicillin, and 100 μg/mL of streptomycin, the human liver cancer cell line was cultured in an incubator at 37° C. and 5% $CO_2$, the human liver cancer cell line was equally dispensed to a 6-well cell culture plate at $9\times10^5$ cell/well, and then, the human liver cancer cell line was further cultured for two days.

Thereafter, before the purified CP-hFGF7$^{115-114}$ protein was treated, cell starvation was performed in a serum-free DMEM medium containing no FBS for 24 hours.

Similar to the method described in 6.1 of Example 6, experimental groups were classified into experimental groups obtained by treating HepG2 cell line experimental groups with 50 ng/mL of the purified CP-hFGF7$^{115-114}$ protein for 30 minutes, 60 minutes, and 120 minutes, and experimental groups obtained by treating the HepG2 cell line experimental groups treated with the CP-hFGF7$^{115-114}$ protein at treatment concentrations of 100, 50, 25, 5, and 1 ng/mL for 30 minutes. Thereafter, the experimental groups were treated with a RIPA buffer solution (25 mM of Tris-HCl, pH 7.6, 150 mM of NaCl, 1% NP-40, 1% sodium deoxycholate, 0.1% SDS, Thermo Fisher Scientific (Waltham, MA, USA)) containing protease inhibitor cocktail (Thermo Fisher Scientific (Waltham, MA, USA)) and phosphatase inhibitor cocktail (Thermo Fisher Scientific (Waltham, MA, USA)) to lyse cells.

Subsequently, a cell lysate was obtained with a scraper, and then, immunoblotting using antibodies against Erk1/2 (Cell Signaling Technology Co. (Danvers, MA, USA)), phosphorylated Erk1/2 (Cell Signaling Technology Co. (Danvers, MA, USA)), and α-tubulin (Santa Cruz Biotechnology Inc. (Dallas, TX, USA)) was performed to analyze activity.

The results are illustrated in FIGS. 10A and 10B.

The treatment concentrations of the purified protein and the positive control group were fixed at 50 ng/mL, and then, the treatment time was changed to 30 minutes, 60 minutes, and 120 minutes. As a result, strong phosphorylation of Erk1/2 was induced with short-term treatment for 30 minutes, and the phosphorylation of Erk1/2 was decreased over time, which was the same as that of rhFGF7 as the positive control group (see FIG. 10A).

In addition, the treatment concentration of the protein was changed to 100, 50, 25, 5, and 1 ng/mL, and the same treatment time was set to 30 minutes. As a result, strong phosphorylation of Erk1/2 was exhibited in all of the purified protein and the positive control group regardless of the concentration. It was confirmed that the level was similar to that of the positive control group treated at the same concentration (see FIG. 10B).

It was confirmed from the above results that in the present invention, the purified CP-hFGF7$^{115-114}$ protein activated the RAS-MARK-ERK signaling pathway in the both mouse-derived and human-derived cell lines at a similar or higher level than that of the wild-type hFGF7 protein, and thus, the CP-hFGF7$^{115-114}$ protein had a high level of a proliferation.

Example 7 Cytotoxicity of Purified CP-hFGF7$^{115-114}$ Protein

Cytotoxicity in the mouse embryonic fibroblast cell line (NIH3T3) was measured as follows using a cell counting kit 8 (WST-8/CCK-8, Abcam (Waltham, MA, USA)).

NIH3T3 was inoculated into a DMEM (Gibco, ThermoFisher Scientific (Waltham, MA, USA)) medium containing 10% bovine calf serum (BC S), 100 μg/mL of penicillin, and 100 μg/mL of streptomycin, and the NIH3T3 was cultured in an incubator at 37° C. and 5% $CO_2$ for 24 hours. When 70 to 80% of the cells grew, each of the purified protein and the positive control group was treated at a concentration of 0.5 to 100 ng/mL.

Subsequently, after the cells were cultured from 24 hours to 72 hours, a color change of a reagent reacting with dehydrogenase in mitochondria, which was an intracellular organelle, was measured at 450 nm using a SpectraMax® ABS microplate reader (Molecular Devices (San Jose, CA, USA)), and comparison of cytotoxicity over time was performed. The cytotoxicity was determined based on cell viability.

The results are illustrated in FIGS. 11A and B.

At the time of culture for 24 hours, in the case of the purified CP-hFGF7$^{115-114}$ protein at a concentration of 50 ng/mL, a high cell viability of 98 to 100% was exhibited, and at the time of culture for 72 hours, in the case of the purified CP-hFGF7$^{115-114}$ protein at a concentration of 100 ng/mL, a high cell viability of 96% was exhibited.

That is, it was confirmed that the purified CP-hFGF7$^{115-114}$ protein according to the present invention had safety because a high cell viability was exhibited and a level of cytotoxicity was similar to that of the wild-type hFGF7 protein.

Example 8 Cell Proliferation Activity of Purified CP-hFGF7$^{115-114}$ Protein The cell proliferation activity of the purified CP-hFGF7$^{115-114}$ protein was compared with that of the wild-type hFGF7 (rhFGF7) protein as the positive control group using the CCK-8 kit and the NIH3T3 cell line used in Example 7.

NIH3T3 was inoculated into a DMEM (Gibco, ThermoFisher Scientific (Waltham, MA, USA)) medium containing 10% bovine calf serum (BC S), 100 μg/mL of penicillin, and 100 μg/mL of streptomycin, and the NIH3T3 was cultured in an incubator at 37° C. and 5% $CO_2$ for 24 hours. When 80% or more of the cells grew, each of the purified protein and the positive control group was treated at a concentration of each of 50, 10, and 1 ng/mL, and culture was performed.

After 10 μL of a CCK-8 solution was added to each well during culture of each of the experimental groups for 24, 48, and 72 hours and additional culture was performed for 3 hours, comparison of cell proliferation activity for each time measured at 460 nm using a SpectraMax® ABS microplate reader (Molecular Devices (San Jose, CA, USA)) was performed.

The results are illustrated in FIGS. 12A and B.

It was confirmed from the results that the CP-hFGF7$^{115-114}$ protein according to the present invention maintained cell proliferation activity similar to that of the wild-type hFGF7 protein.

Example 9 Wound Healing Activity of Purified CP-hFGF7$^{115-114}$ Protein

Based on the cell proliferation activity results in Example 8, scratches in the NIH3T3 cells were induced, and then, comparison of a wound healing effect for the same time was performed as follows.

NIH3T3 was inoculated into a DMEM (Gibco, ThermoFisher Scientific (Waltham, MA, USA)) medium containing 10% bovine calf serum (BC S), 100 μg/mL of penicillin, and 100 μg/mL of streptomycin, and the NIH3T3 was cultured in an incubator at 37° C. and 5% $CO_2$ for 24 hours. When 100% of the cells grew, the cells were scratched using a 10 μL pipette tip to induce wound formation.

After the cells were scratched, the medium was changed to a serum-free DMEM medium containing no BCS in order to remove cell debris.

After each of the purified CP-hFGF7115-114 protein according to the present invention and the wild-type hFGF7 (rhFGF7) protein as the positive control group was treated at a concentration of each of 0, 1, 10, and 50 ng/ml, culture was performed for 0, 24, 48, and 72 hours, and the cells were observed with an optical microscope (Eclipse™ TE2000-E, Nikon).

The results are illustrated in FIG. 13.

It was confirmed from the results that when the purified protein and the positive control group were treated at the same concentration of 50 ng/mL, and then, the cells (marked in the black box) after 72 hours were compared, a cell density in the experimental group treated with the purified CP-hFGF7$^{115-114}$ protein according to the present invention was higher than that of the positive control group, which showed that the wound healing effect of the purified protein according to the present invention was superior to that of the positive control group.

It was confirmed from the results of Examples that in the case of the purified CP-hFGF7$^{115-114}$ protein obtained through the recombinant vector for inducing soluble overexpression of the fibroblast growth factor 7 (FGF7) and the method of preparing a human-derived FGF7 using the same, the activity was equal to or higher than that of the commercially available recombinant hFGF7 (rhFGF7).

Palifermin in which 24 amino acids at the N-terminus are deleted, which is currently marketed for medicinal purposes, is an rhFGF7 variant, and has been used for treating oral mucositis. Palifermin is a medicine developed because hFGF7 (rhFGF7) used as the control group in the experiment has problems due to a low expression level and low stability.

On the other hand, the purified CP-hFGF7$^{115-114}$ protein after soluble expression according to the present invention has significantly excellent stability, a high soluble expression rate, and a simple purification process, and thus, the purified CP-hFGF7$^{115-114}$ protein is expected to be used as a novel drug through the production from mass culture. In addition, the purified CP-hFGF7$^{115-114}$ protein has structural features closer to that of the wild-type protein with no amino acid deletion, and thus, it has an advantage of being able to present solutions for immunological problems.

As set forth above, the fibroblast growth factor 7 to which a circular permutation is applied (CP-hFGF7) is independently expressed in a host cell, such that it is possible to induce soluble overexpression of the fibroblast growth factor 7 without causing problems according to the related art, such as lower expression level and stability compared to those of the wild-type hFGF7 protein and amino acid changes in a process of removing a fusion tag.

Special portions of contents of the present invention have been described in detail hereinabove, and it will be obvious to those skilled in the art that this detailed description is only an exemplary embodiment and the scope of the present invention is not limited by this detailed description. Therefore, the substantial scope of the present invention will be defined by the appended claims and equivalents thereof.

The invention claimed is:

1. A vector comprising a polynucleotide encoding a circular permutated fibroblast growth factor 7 protein variant, wherein the protein variant is CP-hFGF7$^{115-114}$, wherein the polynucleotide encoding the protein variant consists of a base sequence of SEQ ID NO: 3, and wherein the vector consists of a base sequence of SEQ ID NO: 5.

2. The vector of claim 1, wherein the protein variant consists of an amino acid sequence of SEQ ID NO: 4.

3. A transformant transformed with the vector of claim 2.

4. A transformant transformed with the vector of claim 1.

* * * * *

```
                         SEQUENCE LISTING


Sequence total quantity: 31
SEQ ID NO: 1           moltype = DNA  length = 495
FEATURE                Location/Qualifiers
misc_feature           1..495
                       note = Wildtype FGF7
```

-continued

```
source                  1..495
                        mol_type = other DNA
                        organism = synthetic construct
SEQUENCE: 1
atgtgcaatg acatgactcc agagcaaatg gctacaaatg tgaactgttc cagccctgag  60
cgacacacaa gaagttatga ttacatggaa ggaggggata taagagtgag aagactcttc  120
tgtcgaacac agtggtacct gaggatcgat aaaagaggca aagtaaaagg gacccaagag  180
atgaagaata attacaatat catggaaatc aggacagtgg cagttggaat tgtggcaatc  240
aaaggggtgg aaagtgaatt ctatcttgca atgaacaagg aaggaaaact ctatgcaaag  300
aaagaatgca atgaagattg taacttcaaa gaactaattc tggaaaacca ttacaacaca  360
tatgcatcag ctaaatggac acacaacgga ggggaaatgt ttgttgcctt aaatcaaaag  420
gggattcctg taagaggaaa aaaaacgaag aaagaacaaa aaacagccca ctttcttcct  480
atggcaataa cttaa                                                   495

SEQ ID NO: 2            moltype = AA  length = 164
FEATURE                 Location/Qualifiers
REGION                  1..164
                        note = Wildtype FGF7
source                  1..164
                        mol_type = protein
                        organism = synthetic construct
SEQUENCE: 2
MCNDMTPEQM ATNVNCSSPE RHTRSYDYME GGDIRVRRLF CRTQWYLRID KRGKVKGTQE  60
MKNNYNIMEI RTVAVGIVAI KGVESEFYLA MNKEGKLYAK KECNEDCNFK ELILENHYNT  120
YASAKWTHNG GEMFVALNQK GIPVRGKKTK KEQKTAHFLP MAIT                  164

SEQ ID NO: 3            moltype = DNA  length = 495
FEATURE                 Location/Qualifiers
misc_feature            1..495
                        note = CP-hFGF7 115-114
source                  1..495
                        mol_type = other DNA
                        organism = synthetic construct
SEQUENCE: 3
atggaaaacc attacaacac atatgcatca gctaaatgga cacacaacgg aggggaaatg  60
tttgttgcct taaatcaaaa ggggattcct gtaagaggaa aaaaaacgaa gaaagaacaa  120
aaaacagccc actttcttcc tatggcaata acttgcaatg acatgactcc agagcaaatg  180
gctacaaatg tgaactgttc cagccctgag cgacacacaa gaagttatga ttacatggaa  240
ggaggggata taagagtgag aagactcttc tgtcgaacac agtggtacct gaggatcgat  300
aaaagaggca aagtaaaagg gacccaagag atgaagaata attacaatat catggaaatc  360
aggacagtgg cagttggaat tgtggcaatc aaaggggtgg aaagtgaatt ctatcttgca  420
atgaacaagg aaggaaaact ctatgcaaag aaagaatgca atgaagattg taacttcaaa  480
gaactaattc tgtaa                                                   495

SEQ ID NO: 4            moltype = AA  length = 164
FEATURE                 Location/Qualifiers
REGION                  1..164
                        note = CP-hFGF7 115-114
source                  1..164
                        mol_type = protein
                        organism = synthetic construct
SEQUENCE: 4
MENHYNTYAS AKWTHNGGEM FVALNQKGIP VRGKKTKKEQ KTAHFLPMAI TCNDMTPEQM  60
ATNVNCSSPE RHTRSYDYME GGDIRVRRLF CRTQWYLRID KRGKVKGTQE MKNNYNIMEI  120
RTVAVGIVAI KGVESEFYLA MNKEGKLYAK KECNEDCNFK ELIL                  164

SEQ ID NO: 5            moltype = DNA  length = 4827
FEATURE                 Location/Qualifiers
misc_feature            1..4827
                        note = pSCold_CP-hFGF7 115-114
source                  1..4827
                        mol_type = other DNA
                        organism = synthetic construct
SEQUENCE: 5
aaggaatggt gtggccgatt aatcataaat atgaaaaata attgttgcat cacccgccaa  60
tgcgtggctt aatgcacatc aaattgtgag cggataacaa tttgatgtgc tagcgcatat  120
ccagtgtagt aaggcaagtc ccttcaagag ttatcgttga taccccctcgt agtgcacatt  180
cctttaacgc ttcaaaatct gtaaagcacg ccatatcgcc gaaaggcaca cttaattatt  240
aagaggtaat acaccactag tatggaaaac cattacaaca catatgcatc agctaaatgg  300
acacacaacg gaggggaaat gtttgttgcc ttaaatcaaa aggggattcc tgtaagagga  360
aaaaaaacga agaaagaaca aaaaacagcc cactttcttc ctatggcaat aacttgcaat  420
gacatgactc cagagcaaat ggctacaaat gtgaactgtt ccagccctga gcgacacaca  480
agaagttatg attacatgga aggaggggat ataagagtga gaagactctt ctgtcgaaca  540
cagtggtacc tgaggatcga taaaagaggc aaagtaaaag ggacccaaga gatgaagaat  600
aattacaata tcatggaaat caggacagtg gcagttggaa ttgtggcaat caaaggggtg  660
gaaagtgaat tctatcttgc aatgaacaag gaaggaaaac tctatgcaaa gaaagaatgc  720
aatgaagatt gtaacttcaa agaactaatt ctgtaaaagc ttgtcgacct gcagtctaga  780
taggtaatct ctgcttaaaa gcacagaatc taagatccct gccatttggc ggggattttt  840
ttatttgttt tcaggaaata aataatcgat cgcgtaataa aatctattat tatttttgtg  900
```

```
aagaataaat ttgggtgcaa tgagaatgcg caggcccttt cgtctcgcgc gtttcggtga  960
tgacggtgaa aacctctgac acatgcagct cccggagacg gtcacagctt gtctgtaagc  1020
ggatgccggg agcagacaag cccgtcaggg cgcgtcagcg ggtgttggcg ggtgtcgggg  1080
ctggcttaac tatgcggcat cagagcagat tgtactgaga gtgcaccata aaattgtaaa  1140
cgttaatatt ttgttaaaat tcgcgttaaa tttttgttaa atcagctcat tttttaacca  1200
ataggccgaa atcggcaaaa tcccttataa atcaaaagaa tagcccgaga tagggttgag  1260
tgttgttcca gtttggaaca agagtccact attaaagaac gtggactcca acgtcaaagg  1320
gcgaaaaacc gtctatcagg gcgatggccc actacgtgaa ccatcaccca aatcaagttt  1380
tttggggtcg aggtgccgta aagcactaaa tcggaaccct aaagggagcc cccgatttag  1440
agcttgacgg ggaaagccgg cgaacgtggc gagaaaggaa gggaagaaag cgaaaggagc  1500
gggcgctagg gcgctggcaa gtgtagcggt cacgctgcgc gtaaccacca cacccgccgc  1560
gcttaatgcg ccgctacagg gcgcgtacta tggttgcttt gacgtatgcg gtgtgaaata  1620
ccgcacagat gcgtaaggag aaaataccgc atcaggcgtc aggtggcact tttcggggaa  1680
atgtgcgcgg aacccctatt tgtttatttt tctaaataca ttcaaatatg tatccgctca  1740
tgagacaata accctgataa atgcttcaat aatattgaaa aaggaagagt atgagtattc  1800
aacatttccg tgtcgccctt attccctttt ttgcggcatt ttgccttcct gtttttgctc  1860
acccagaaac gctggtgaaa gtaaaagatg ctgaagatca gttgggtgca cgagtgggtt  1920
acatcgaact ggatctcaac agcggtaaga tccttgagag ttttcgcccc gaagaacgtt  1980
ttccaatgat gagcactttt aaagttctgc tatgtggcgc ggtattatcc cgtattgacg  2040
ccgggcaaga gcaactcggt cgccgcatac actattctca gaatgacttg gttgagtact  2100
caccagtcac agaaaagcat cttacggatg gcatgacagt aagagaatta tgcagtgctg  2160
ccataaccat gagtgataac actgcggcca acttacttct gacaacgatc ggaggaccga  2220
aggagctaac cgcttttttg cacaacatgg gggatcatgt aactcgcctt gatcgttggg  2280
aaccggagct gaatgaagcc ataccaaacg acgagcgtga caccacgatg cctgtagcaa  2340
tggcaacaac gttgcgcaaa ctattaactg gcgaactact tactctagct tcccggcaac  2400
aattaataga ctggatggag gcggataaag ttgcaggacc acttctgcgc tcggcccttc  2460
cggctggctg gtttattgct gataaatctg gagccggtga gcgtgggtct cgcggtatca  2520
ttgcagcact ggggccagat ggtaagccct cccgtatcgt agttatctac acgacgggga  2580
gtcaggcaac tatggatgaa cgaaatagac agatcgctga gataggtgcc tcactgatta  2640
agcattggta actgtcagac caagtttact catatatact ttagattgat ttaaaacttc  2700
atttttaatt taaaaggatc taggtgaaga tcctttttga taatctcatg accaaaatcc  2760
cttaacgtga gttttcgttc cactgagcgt cagaccccgt agaaaagatc aaaggatctt  2820
cttgagatcc tttttttctg cgcgtaatct gctgcttgca aacaaaaaaa ccaccgctac  2880
cagcggtggt ttgtttgccg gatcaagagc taccaactct ttttccgaag gtaactggct  2940
tcagcagagc gcagatacca aatactgttc ttctagtgta gccgtagtta ggccaccact  3000
tcaagaactc tgtagcaccg cctacatacc tcgctctgct aatcctgtta ccagtggctg  3060
ctgccagtgg cgataagtcg tgtcttaccg ggttggactc aagacgatag ttaccggata  3120
aggcgcagcg gtcgggctga acggggggtt cgtgcacaca gcccagcttg gagcgaacga  3180
cctacaccga actgagatac ctacagcgtg agctatgaga aagcgccacg cttcccgaag  3240
ggagaaaggc ggacaggtat ccggtaagcg gcagggtcgg aacaggagag cgcacgaggg  3300
agcttccagg gggaaacgcc tggtatcttt atagtcctgt cgggtttcgc cacctctgac  3360
ttgagcgtcg atttttgtga tgctcgtcag gggggcggag cctatggaaa aacgccagca  3420
acgcggcctt tttacggttc ctggcctttt gctggccttt tgctcacata gtcatgcccc  3480
gcgcccaccg gaaggagctg actgggttga aggctctcaa gggcatcggt cgagatcccg  3540
gtgcctaatg agtgagctaa cttacattaa ttgcgttgcg ctcactgccc gctttccagt  3600
cgggaaacct gtcgtgccag ctgcattaat gaatcggcca acgcgcgggg agaggcggtt  3660
tgcgtattgg gcgccagggt ggtttttctt ttcaccagtg agacgggcaa cagctgattg  3720
cccttcaccg cctggccctg agagagttgc agcaagcggt ccacgctggt ttgccccagc  3780
aggcgaaaat cctgtttgat ggtggttaac ggcgggatat aacatgagct gtcttcggta  3840
tcgtcgtatc ccactaccga gatatccgca ccaacgcgca gcccggactc ggtaatggcg  3900
cgcattgcgc ccagcgccat ctgatcgttg gcaaccagca tcgcagtggg aacgatgccc  3960
tcattcagca tttgcatggt ttgttgaaaa ccggacatgg cactccagtc gccttcccgt  4020
tccgctatcg gctgaatttg attgcgagtg agatatttat gccagccagc cagacgcaga  4080
cgcgccgaga cagaacttaa tgggcccgct aacagcgcga tttgctggtg acccaatgcg  4140
accagatgct ccacgcccag tcgcgtaccg tcttcatggg agaaaataat actgttgatg  4200
ggtgtctggt cagagacatc aagaaataac gccggaacat tagtgcaggc agcttccaca  4260
gcaatggcat cctggtcatc cagcggatag ttaatgatca gcccactgac gcgttgcgcg  4320
agaagattgt gcaccgccgc tttacaggct tcgacgccgc ttcgttctac catcgacacc  4380
accacgctgg cacccagttg atcggcgcga gatttaatcg ccgcgacaat ttgcgacggc  4440
gcgtgcaggg ccagactgga ggtggcaacg ccaatcagca acgactgttt gcccgccagt  4500
tgttgtgcca cgcggttggg aatgtaattc agctccgcca tcgccgcttc cacttttttcc 4560
cgcgttttcg cagaaacgtg gctggcctgg ttcaccacgc gggaaacggt ctgataagag  4620
acaccggcat actctgcgac atcgtataac gttactggtt tcacattcac caccctgaat  4680
tgactctctt ccgggcgcta tcatgccata ccgcgaaagg ttttgcgcca ttcgatggtg  4740
tccgggatct cgacgctctc ccttatgcga ctcctgcatt aggaagcagc ccagtagtag  4800
gttgaggccg ttgagcaccg ccgccgc                                      4827

SEQ ID NO: 6           moltype = DNA  length = 43
FEATURE                Location/Qualifiers
misc_feature           1..43
                       note = pSCT5_hFGF7-Infu-F
source                 1..43
                       mol_type = other DNA
                       organism = synthetic construct
SEQUENCE: 6
taaagaggag aaaactagta tgtgcaatga catgactcca gag                    43

SEQ ID NO: 7           moltype = DNA  length = 33
FEATURE                Location/Qualifiers
```

```
misc_feature          1..33
                      note = hFGF7-Infu-R
source                1..33
                      mol_type = other DNA
                      organism = synthetic construct
SEQUENCE: 7
cattgcaagt tattgccata ggaagaaagt ggg                            33

SEQ ID NO: 8          moltype = DNA  length = 38
FEATURE               Location/Qualifiers
misc_feature          1..38
                      note = hFGF7(X2)-Infu-F
source                1..38
                      mol_type = other DNA
                      organism = synthetic construct
SEQUENCE: 8
tggcaataac ttgcaatgac atgactccag agcaaatg                       38

SEQ ID NO: 9          moltype = DNA  length = 49
FEATURE               Location/Qualifiers
misc_feature          1..49
                      note = pSCT5_hFGF7(X2)-Infu-R
source                1..49
                      mol_type = other DNA
                      organism = synthetic construct
SEQUENCE: 9
agctcagcta attaagcttt taagttattg ccataggaag aaagtgggc           49

SEQ ID NO: 10         moltype = DNA  length = 20
FEATURE               Location/Qualifiers
misc_feature          1..20
                      note = pSCold_Vec-Infu-F
source                1..20
                      mol_type = other DNA
                      organism = synthetic construct
SEQUENCE: 10
aagcttgtcg acctgcagtc                                           20

SEQ ID NO: 11         moltype = DNA  length = 36
FEATURE               Location/Qualifiers
misc_feature          1..36
                      note = pSCold_Vec-Infu-R
source                1..36
                      mol_type = other DNA
                      organism = synthetic construct
SEQUENCE: 11
actagtggtg tattacctct taataattaa gtgtgc                         36

SEQ ID NO: 12         moltype = DNA  length = 42
FEATURE               Location/Qualifiers
misc_feature          1..42
                      note = wt-hFGF7-F
source                1..42
                      mol_type = other DNA
                      organism = synthetic construct
SEQUENCE: 12
aggtaataca ccactagtat gtgcaatgac atgactccag ag                  42

SEQ ID NO: 13         moltype = DNA  length = 47
FEATURE               Location/Qualifiers
misc_feature          1..47
                      note = wt-hFGF7-R
source                1..47
                      mol_type = other DNA
                      organism = synthetic construct
SEQUENCE: 13
ctgcaggtcg acaagctttt aagttattgc cataggaaga aagtggg             47

SEQ ID NO: 14         moltype = DNA  length = 49
FEATURE               Location/Qualifiers
misc_feature          1..49
                      note = pSCold_CP1-hFGF7-F
source                1..49
                      mol_type = other DNA
                      organism = synthetic construct
SEQUENCE: 14
aggtaataca ccactagtat ggatataaga gtgagaagac tcttctgtc           49

SEQ ID NO: 15         moltype = DNA  length = 53
```

```
FEATURE                  Location/Qualifiers
misc_feature             1..53
                         note = pSCold_CP1-hFGF7-R
source                   1..53
                         mol_type = other DNA
                         organism = synthetic construct
SEQUENCE: 15
ctgcaggtcg acaagctttt accctccttc catgtaatca taactagtta ttg         53

SEQ ID NO: 16            moltype = DNA  length = 39
FEATURE                  Location/Qualifiers
misc_feature             1..39
                         note = pSCold_CP2-hFGF7-F
source                   1..39
                         mol_type = other DNA
                         organism = synthetic construct
SEQUENCE: 16
aggtaataca ccactagtat gcgaacacag tggtacctg                         39

SEQ ID NO: 17            moltype = DNA  length = 50
FEATURE                  Location/Qualifiers
misc_feature             1..50
                         note = pSCold_CP2-hFGF7-R
source                   1..50
                         mol_type = other DNA
                         organism = synthetic construct
SEQUENCE: 17
ctgcaggtcg acaagctttt aacagaagag tcttctcact cttatatccc             50

SEQ ID NO: 18            moltype = DNA  length = 46
FEATURE                  Location/Qualifiers
misc_feature             1..46
                         note = pSCold_CP3-hFGF7-F
source                   1..46
                         mol_type = other DNA
                         organism = synthetic construct
SEQUENCE: 18
aggtaataca ccactagtat gaaaagaggc aaagtaaaag ggaccc                 46

SEQ ID NO: 19            moltype = DNA  length = 44
FEATURE                  Location/Qualifiers
misc_feature             1..44
                         note = pSCold_CP3-hFGF7-R
source                   1..44
                         mol_type = other DNA
                         organism = synthetic construct
SEQUENCE: 19
ctgcaggtcg acaagctttt aatcgatcct caggtaccac tgtg                   44

SEQ ID NO: 20            moltype = DNA  length = 53
FEATURE                  Location/Qualifiers
misc_feature             1..53
                         note = pSCold_CP4-hFGF7-F
source                   1..53
                         mol_type = other DNA
                         organism = synthetic construct
SEQUENCE: 20
aggtaataca ccactagtat gaagaataat tacaatatca tggaaatcag gac         53

SEQ ID NO: 21            moltype = DNA  length = 44
FEATURE                  Location/Qualifiers
misc_feature             1..44
                         note = pSCold_CP4-hFGF7-R
source                   1..44
                         mol_type = other DNA
                         organism = synthetic construct
SEQUENCE: 21
ctgcaggtcg acaagctttt actcttgggt cccttttact ttgc                   44

SEQ ID NO: 22            moltype = DNA  length = 46
FEATURE                  Location/Qualifiers
misc_feature             1..46
                         note = pSCold_CP5-hFGF7-F
source                   1..46
                         mol_type = other DNA
                         organism = synthetic construct
SEQUENCE: 22
aggtaataca ccactagtat ggcagttgga attgtggcaa tcaaag                 46
```

```
SEQ ID NO: 23           moltype = DNA  length = 55
FEATURE                 Location/Qualifiers
misc_feature            1..55
                        note = pSCold_CP5-hFGF7-R
source                  1..55
                        mol_type = other DNA
                        organism = synthetic construct
SEQUENCE: 23
ctgcaggtcg acaagctttt acactgtcct gatttccatg atattgtaat tattc       55

SEQ ID NO: 24           moltype = DNA  length = 56
FEATURE                 Location/Qualifiers
misc_feature            1..56
                        note = pSCold_CP6-hFGF7-F
source                  1..56
                        mol_type = other DNA
                        organism = synthetic construct
SEQUENCE: 24
aggtaataca ccactagtat ggaaagtgaa ttctatcttt gtatgaacaa ggaagg      56

SEQ ID NO: 25           moltype = DNA  length = 44
FEATURE                 Location/Qualifiers
misc_feature            1..44
                        note = pSCold_CP6-hFGF7-R
source                  1..44
                        mol_type = other DNA
                        organism = synthetic construct
SEQUENCE: 25
ctgcaggtcg acaagctttt acaccccttt gattgccaca attc                   44

SEQ ID NO: 26           moltype = DNA  length = 49
FEATURE                 Location/Qualifiers
misc_feature            1..49
                        note = pSCold_CP7-hFGF7-F
source                  1..49
                        mol_type = other DNA
                        organism = synthetic construct
SEQUENCE: 26
aggtaataca ccactagtat gaaggaagga gaactctatg caaagaaag              49

SEQ ID NO: 27           moltype = DNA  length = 52
FEATURE                 Location/Qualifiers
misc_feature            1..52
                        note = pSCold_CP7-hFGF7-R
source                  1..52
                        mol_type = other DNA
                        organism = synthetic construct
SEQUENCE: 27
ctgcaggtcg acaagctttt agttcataca aagatagaat tcactttcca cc          52

SEQ ID NO: 28           moltype = DNA  length = 50
FEATURE                 Location/Qualifiers
misc_feature            1..50
                        note = pSCold_CP8-hFGF7-F
source                  1..50
                        mol_type = other DNA
                        organism = synthetic construct
SEQUENCE: 28
aggtaataca ccactagtat ggaaaaccat tacaacacat atgcatcagc             50

SEQ ID NO: 29           moltype = DNA  length = 56
FEATURE                 Location/Qualifiers
misc_feature            1..56
                        note = pSCold_CP8-hFGF7-R
source                  1..56
                        mol_type = other DNA
                        organism = synthetic construct
SEQUENCE: 29
ctgcaggtcg acaagctttt acagaattag ttctttgaag ttacaatctt cattgc      56

SEQ ID NO: 30           moltype = DNA  length = 49
FEATURE                 Location/Qualifiers
misc_feature            1..49
                        note = pSCold_CP9-hFGF7-F
source                  1..49
                        mol_type = other DNA
                        organism = synthetic construct
SEQUENCE: 30
aggtaataca ccactagtat gcaaaagggg attcctgtaa gaggaaaag              49
```

-continued

```
SEQ ID NO: 31           moltype = DNA  length = 47
FEATURE                 Location/Qualifiers
misc_feature            1..47
                        note = pSCold_CP9-hFGF7-R
source                  1..47
                        mol_type = other DNA
                        organism = synthetic construct
SEQUENCE: 31
ctgcaggtcg acaagctttt aatttaaggc aacaaacatt tcccctc               47
```